United States Patent [19]

Shibata et al.

[11] Patent Number: 5,587,484

[45] Date of Patent: Dec. 24, 1996

[54] PYRAZOLE PROCESS AND INTERMEDIATES

[75] Inventors: Mitsuru Shibata; Masashi Sakamoto; Ichiro Nasuno, all of Sodegaura, Japan

[73] Assignee: Idemitsu Kosan Co., Ltd., Tokyo, Japan

[21] Appl. No.: 509,963

[22] Filed: Aug. 1, 1995

Related U.S. Application Data

[62] Division of Ser. No. 290,943, filed as PCT/JP93/00274, Mar. 3, 1993, Pat. No. 5,468,722.

Foreign Application Priority Data

Mar. 3, 1992 [JP] Japan ..................... 4-045821

[51] Int. Cl.⁶ ..................... C07D 335/06; C07D 409/06
[52] U.S. Cl. ..................... 548/364.4; 549/23
[58] Field of Search ..................... 548/364.4; 549/23

[56] References Cited

U.S. PATENT DOCUMENTS

| | | |
|---|---|---|
| 4,885,022 | 1/1989 | Baba et al. . |
| 4,948,887 | 8/1990 | Baba et al. . |
| 4,986,845 | 1/1991 | Oya et al. . |
| 5,175,299 | 12/1992 | Baba et al. . |
| 5,480,858 | 1/1996 | Sakamoto et al. ............ 549/23 |

FOREIGN PATENT DOCUMENTS

| | | |
|---|---|---|
| 49-116071 | 11/1974 | Japan . |
| 2-173 | 1/1990 | Japan . |
| 2-288866 | 11/1990 | Japan . |

*Primary Examiner*—Robert W. Ramsuer
*Attorney, Agent, or Firm*—Frishauf, Holtz, Goodman, Langer & Chick, P.C.

[57] ABSTRACT

Processes for producing a pyrazole compound by reacting a compound

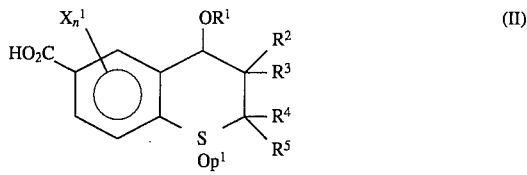

wherein $R^1$ is a $C_1$–$C_6$ alkyl, each of $R^2$, $R^3$, $R^4$ and $R^5$ is hydrogen or a $C_1$–$C_4$ alkyl, $X^1$ is a $C_1$–$C_4$ alkyl or a halogen, n is 1 to 3, and $p^1$ is 0 to 2, with a compound

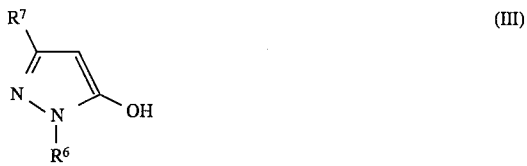

wherein $R^6$ is a $C_1$–$C_4$ alkyl and
$R^7$ is hydrogen or a $C_1$–$C_4$ alkyl, to form a pyrazole compound

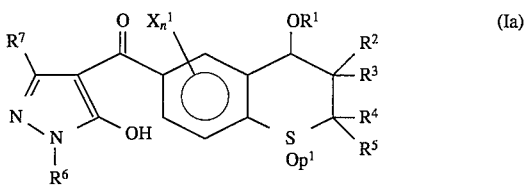

and optionally reacting the pyrazole compound (Ia) with a sulfonic acid halide of the formula $Q^2X^2$ (IV)
wherein $Q^2$ is —$SO_2$—$R^8$ or

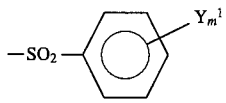

in which $R^8$ is a $C_1$–$C_6$ alkyl, Y is hydrogen, a $C_1$–$C_1$ alkyl or a halogen, $m^1$ is 1 to 3, and $X^2$ is a halogen. Alternatively, the compound of the formula (II) is reacted with a halogenation agent to produce a compound which is reacted with a compound of the formula (III) to produce a compound which is heated to form a compound of the formula (Ia).

17 Claims, No Drawings

PYRAZOLE PROCESS AND INTERMEDIATES

This is a division of application Ser. No. 08/290,943 filed Aug. 23, 1994 now U.S. Pat. No. 5,468,722, which is the United States designated application of PCT/JP93/00274 filed Mar. 3, 1993.

TECHNICAL FIELD

The present invention relates to pyrazole derivatives. More specifically, it relates to novel pyrazole derivatives, a process for the production thereof, herbicides containing them as active ingredients, and novel intermediate compounds suitable for the production thereof.

TECHNICAL BACKGROUND

During a growing period of corn, etc., a triazine-based herbicide such as atrazine and acid anilide-based herbicides such as alachlor and metolachlor have been conventionally used, while atrazine shows low efficacy to gramineous weeds, and arachlor and metolachlor show low efficacy to broad-leaved weeds. It is therefore difficult at present to control gramineous weeds and broad-leaved weeds at the same time with a single herbicide. Further, the above herbicides are undesirable in view of an environmental problem due to their high dosage requirement.

On the other hand, it is known that specific 4-benzoyl-pyrazole derivatives have herbicidal activity (see JP-A-63-122672, JP-A-63-122673, JP-A-63-170365, JP-A-1-52759, JP-A-2-173 and JP-A-2-288866). Further, for example, pyrazolate of the following formula is known as a commercial herbicide.

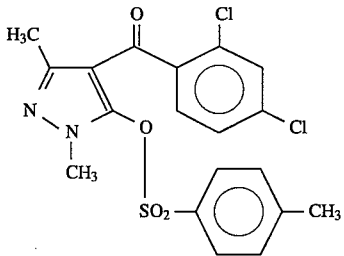

However, pyrazole derivatives having a thiochroman ring such as compounds of the present invention have not yet been known so far.

Further, the commercially available herbicide, pyrazolate, is for use in a paddy field, and it hardly has herbicidal activity when used in a plowed field. Further, 4-benzoyl-pyrazole derivatives that have been already disclosed are insufficient in practical use although they have herbicidal activity in a plowed field. For example, the 4-benzoyl-pyrazole derivatives disclosed in JP-A-63-122872 have activity to broad-leaved weeds such as cocklebur, velvetleaf, slender amaranth, etc., When used for foliar treatment, while the activity thereof is practically insufficient. Further, they show very poor activity to gramineous weeds such as green foxtail, large crabgrass, barnyardgrass, etc. In soil treatment, the above derivatives show activity to gramineous weeds such as green foxtail, large crabgrass, barnyardgrass, etc., while they show very poor activity to broad-leaved weeds such as cocklebur, velvetleaf, slender amaranth, etc.

DISCLOSURE OF THE INVENTION

It is an object of the present invention, in a broad sense, to provide a novel pyrazole derivative which shows high selectivity to corn, wheat and barley and which can control gramineous weeds and broad-leaved weeds at low dosage by any one of foliar treatment and soil treatment. More specifically, it is an object of the present invention to provide the above novel pyrazole derivative, a process for the production thereof, a herbicide containing the same as an active ingredient, and a novel intermediate compound suitable for the production thereof.

The novel pyrazole derivative of the present invention is a compound of the general, formula (I).

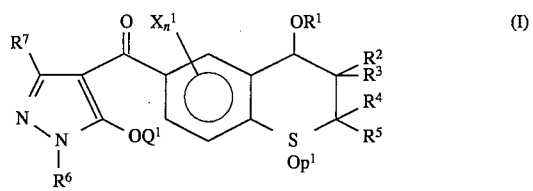

PREFERRED EMBODIMENTS FOR WORKING THE INVENTION

In the general formula (I) for the novel pyrazole derivative of the present invention, $R^1$ is a $C_1$–$C_6$ alkyl group such as methyl, ethyl, propyl, butyl, pentyl or hexyl, and each of the propyl, butyl, pentyl and hexyl may be linear or branched. $R^1$ is preferably a $C_1$–$C_4$ alkyl group, more preferably methyl, ethyl or i-propyl.

Each of $R^2$, $R^3$, $R^4$ and $R^5$ is independently hydrogen or a $C_1$–$C_4$ alkyl group. The $C_1$–$C_4$ alkyl includes methyl, ethyl, propyl and butyl, and the propyl and butyl may be linear or branched. Each of $R^2$, $R^3$, $R^4$ and $R^5$ is preferably hydrogen or methyl, more preferably hydrogen.

$R^6$ is a $C_1$–$C_4$ alkyl group, and specific examples thereof include those described concerning the above $R^2$. $R^6$ is preferably methyl or ethyl.

$R^7$ is hydrogen or a $C_1$–$C_4$ alkyl group, and the $C_1$–$C_4$ alkyl group includes those described concerning the above $R^2$. $R^7$ is preferably hydrogen or methyl.

$X^1$ is a $C_1$–$C_4$ alkyl group or a halogen atom, and the former $C_1$–$C_4$ alkyl group includes those described concerning the above $R^2$. The latter halogen atom includes chlorine, bromine, iodine and fluorine. $X^1$ is preferably a $C_1$–$C_4$ alkyl group, more preferably methyl.

n is a number of $X^1$, and it is an integer of 1 to 3. When n is 2 or 3, a plurality of $X^1$s may be the same or different from, each other. Preferably, n is 1 or 2, and preferably, $X^1$ is substituted on the 5-position or $X^1$s are substituted on the 5-position and 8-position.

$p^1$ is a number of oxygen atom(s) bonding to the sulfur atom, and it is an integer of 0 to 2. When $p^1$=0, sulfide is represented. When $p^1$=1, sulfoxide is represented. When $p^1$=2, sulfone is represented. $p^1$ is preferably 1 (sulfoxide) or 2 (sulfone), more preferably 2 (sulfone).

$Q^1$ is hydrogen. —$SO_2$—$R^8$ or

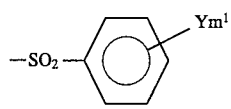

In the former sulfonyl group, $-SO_2-R^8$, $R^8$ is a $C_1-C_6$ alkyl group, and specific examples thereof include those described concerning the above $R^1$. $R^8$ is preferably ethyl, n-propyl or i-propyl. In the latter sulfonyl group,

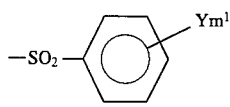

Y is hydrogen, a $C_1-C_4$ alkyl group or a halogen atom. The $C_1-C_4$ alkyl group includes chose described concerning the above $R^2$, and the halogen atom includes those described concerning the above $X^1$. $m^1$ is a number of Y, and it is an integer of 1 to 3. When $m^1$ is 2 or 3, a plurality of Ys may be the same as, or different from, each other. Preferably, $m^1$ is 1 or 2.

Specific examples of the pyrazole derivative of the general formula (I) are preferably as follows.

TABLE 1

| Structural formula | Name |
| --- | --- |
|  | 4-Methoxy-5-methyl-6-(1-ethyl-5-hydroxypyrazol-4-yl)carbonylthiochroman-1,1-dioxide |
|  | 8-Fluoro-4-methoxy-5-methyl-6-(1-ethyl-5-hydroxypyrazol-4-yl)carbonylthiochroman-1,1-dioxide |
|  | 5,8-Dichloro-4-methoxy-6-(1-ethyl-5-hydroxypyrazol-4-yl)carbonylthiochroman-1,1-dioxide |
|  | 8-Fluoro-4-methoxy-5-methyl-6-(1-ethyl-5-methanesulfonyloxypyrazol-4-yl)-carbonylthiochroman-1,1-dioxide |
|  | 8-Fluoro-4-methoxy-5-methyl-6-(1-ethyl-5-p-toluenesufonyloxypyrazol-4-yl)carbonylthiochroman-1,1-dioxide |
|  | 8-Fluoro-4-methoxy-2,5-dimethyl-6-(1-ethyl-5-hydroxypyrazol-4-yl)-carbonylthiochroman-1,1-dioxide |

TABLE 1-continued

| Structural formula | Name |
|---|---|
| | 5,8-Dichloro-4-methoxy-6-(1,3-dimethyl-5-hydroxy-pyrazol-4-yl)-carbonyl-thiochroman-1,1-dioxide |
| | 8-Chloro-4-methoxy-5-methyl-6-(1-ethyl-5-hydroxypyrazol-4-yl)carbonylthiochroman-1,1-dioxide |
| | 8-Fluoro-4-methoxy-5-methyl-6-(1,3-dimethyl-5-hydroxy-pyrazol-4-yl)carbonyl-thiochroman-1,1-dioxide |
| | 4-Methoxy-5-methyl-6-(1,3-dimethyl-5-hydroxy-pyrazol-4-yl)carbonyl-thiochroman-1,1-dioxide |
| | 4-Methoxy-5-methyl-6-(1-methyl-5-hydroxypyrazol-4-yl)carbonylthiochroman-1,1-dioxide |
| | 4-Methoxy-5-methyl-6-(1-ethyl-5-methanesulfonyloxy-pyrazol-4-yl)carbonyl-thiochroman-1,1-dioxide |
| | 4-Methoxy-5-methyl-6-(1-ethyl-5-p-toluenesulfonyl-oxypyrazol-4-yl)carbonyl-thiochroman-1,1-dioxide |
| | 4-Methoxy-2,5-dimethyl-6-(1-ethyl-5-hydroxypyrazol-4-yl)carbonylthiochroman-1,1-dioxide |

TABLE 1-continued

| Structural formula | Name |
|---|---|
| | 4-Methoxy-2,2,5-trimethyl-6-(1-ethyl-5-hydroxypyrazol-4-yl)carbonylthiochroman-1,1-dioxide |
| | 4-Methoxy-3,5-dimethyl-6-(1-ethyl-5-hydroxypyrazol-4-yl)carbonylthiochroman-1,1-dioxide |
| | 4-Methoxy-3,3,5-trimethyl-6-(1-ethyl-5-hydroxypyrazol-4-yl)carbonylthiochroman-1,1-dioxide |
| | 4-Ethoxy-5-methyl-6-(1-ethyl-5-hydroxypyrazol-4-yl)carbonylthiochroman-1,1-dioxide |
| | 4-Isopropoxy-5-methyl-6-(1-ethyl-5-hydroxypyrazol-4-yl)carbonylthiochroman-1,1-dioxide |
| | 4-Methoxy-5,8-dimethyl-6-(1-ethyl-5-hydroxypyrazol-4-yl)carbonylthiochroman-1,1-dioxide |
| | 5-Chloro-4-methoxy-6-(1-ethyl-5-hydroxypyrazol-4-yl)carbonylthiochroman-1,1-dioxide |
| | 5-Fluoro-4-methoxy-6-(1-ethyl-5-hydroxypyrazol-4-yl)carbonylthiochroman-1,1-dioxide |

TABLE 1-continued

| Structural formula | Name |
|---|---|
| | 5-Bromo-4-methoxy-6-(1-ethyl-5-hydroxypyrazol-4-yl)carbonylthiochroman-1,1-dioxide |
| | 4-Methoxy-5-methyl-6-(5-ethylsulfonyloxy-1-ethyl-pyrazol-4-yl)carbonyl-thiochroman-1,1-dioxide |
| | 4-Methoxy-5-methyl-6-(1-ethyl-5-n-propylsulfonyl-oxypyrazol-4-yl)carbonyl-thiochroman-1,1-dioxide |
| | 4-Methoxy-5-methyl-6-(5-i-butylsulfonyloxy-1-ethyl-pyrazol-4-yl)carbonyl-thiochroman-1,1-dioxide |
| | 4-Methoxy-5-methyl-6-(1-ethyl-5-i-propylsulfonyl-oxypyrazol-4-yl)carbonyl-thiochroman-1,1-dioxide |
| | 4-Methoxy-5-methyl-6-(5-phenylsulfonyloxy-1-ethyl-pyrazol-4-yl)carbonyl-thiochroman-1,1-dioxide |
| | 4-Methoxy-5-methyl-6-(5-(4-chlorophenyl)sulfonyloxy-1-ethylpyrazol-4-yl)-carbonylthiochroman-1,1-dioxide |

TABLE 1-continued

| Structural formula | Name |
|---|---|
| (structure) | 4-n-Propoxy-5-methyl-6-(1-ethyl-5-hydroxypyrazol-4-yl)carbonylthiochroman-1,1-dioxide |
| (structure) | 4-Methoxy-5-methyl-6-(1-ethyl-5-hydroxypyrazol-4-yl)carbonylthiochroman |
| (structure) | 4-Methoxy-5-methyl-6-(1-i-propyl-5-hydroxypyrazol-4-yl)carbonylthiochroman-1,1-dioxide |
| (structure) | 8-Fluoro-4-methoxy-5-methyl-6-(1-ethyl-5-n-propyl-sulfonyloxypyrazol-4-yl)-carbonylthiochroman-1,1-dioxide |
| (structure) | 8-Fluoro-4-methoxy-5-methyl-6-(5-phenylsulfonyl-oxy-1-ethylpyrazol-4-yl)-carbonylthiochroman-1,1-dioxide |
| (structure) | 8-Fluoro-4-methoxy-2,5-dimethyl-6-(5-hydroxy-1,3-dimethylpyrazol-4-yl)-carbonylthiochroman-1,1-dioxide |
| (structure) | 8-Fluoro-4-methoxy-2,5-dimethyl-6-(1-ethyl-5-hydroxypyrazol-4-yl)-carbonylthiochroman |

TABLE 1-continued

| Structural formula | Name |
|---|---|
| | 4-Ethoxy-8-fluoro-2,5-dimethyl-6-(1-ethyl-5-hydroxypyrazol-4-yl)-carbonylthiochroman |
| | 4-Ethoxy-8-fluoro-2,5-dimethyl-6-(1-ethyl-5-hydroxypyrazol-4-yl)-carbonylthiochroman-1,1-dioxide |
| | 4-Methoxy-5,8-dimethyl-6-(5-ethylsulfonyloxy-1-ethylpyrazol-4-yl)carbonyl-thiochroman-1,1-dioxide |
| | 4-Methoxy-5,8-dimethyl-6-(1-ethyl-5-n-propylsulfonyl-oxypyrazol-4-yl)carbonyl-thiochroman-1,1-dioxide |
| | 4-Methoxy-5,8-dimethyl-6-(5-i-butylsulfonyloxy-1-ethylpyrazol-4-yl)-carbonylthiochroman-1,1-dioxide |
| | 4-Methoxy-5,8-dimethyl-6-(5-phenylsulfonyloxy-1-ethylpyrazol-4-yl)carbonyl-thiochroman-1,1-dioxide |
| | 4-Methoxy-5,8-dimethyl-6-(1-ethyl-5-p-toluene-sulfonyloxypyrazol-4-yl)-carbonylthiochroman-1,1-dioxide |

TABLE 1-continued

| Structural formula | Name |
|---|---|
| | 4-Methoxy-5,8-dimethyl-6-(5-(4-chlorophenyl)sulfonyloxy-1-ethylpyrazol-4-yl)-carbonylthiochroman-1,1-dioxide |
| | 4-Methoxy-5,8-dimethyl-6-(5-(2,5-dichlorophenyl)-sulfonyloxy-1-ethylpyrazol-4-yl)carbonylthiochroman-1,1-dioxide |
| | 4-Methoxy-5,8-dimethyl-6-(1-ethyl-5-n-propylsulfonyloxypyrazol-4-yl)carbonylthiochroman-1,1-dioxide |
| | 4-Methoxy-5,8-dimethyl-6-(5-(4-chlorophenyl)sulfonyloxy-1-ethylpyrazol-4-yl)-carbonylthiochroman |
| | 4-Methoxy-5,8-dimethyl-6-(1-ethyl-5-hydroxypyrazol-4-yl)carbonylthiochroman |
| | 4-Ethoxy-5,8-dimethyl-6-(1-ethyl-5-p-toluenesulfonyloxypyrazol-4-yl)-carbonylthiochroman-1,1-dioxide |

TABLE 1-continued

| Structural formula | Name |
| --- | --- |
|  | 4-Ethoxy-5,8-dimethyl-6-(1-ethyl-5-hydroxypyrazol-4-yl)carbonylthiochroman-1,1-dioxide |
|  | 4-Ethoxy-5,8-dimethyl-6-(1-ethyl-5-hydroxypyrazol-4-yl)carbonylthiochroman |
|  | 4-n-Butoxy-5,8-dimethyl-6-(1-ethyl-5-hydroxypyrazol-4-yl)carbonylthiochroman-1,1-dioxide |
|  | 4-Methoxy-5,8-dimethyl-6-(5-hydroxy-1,3-dimethylpyrazol-4-yl)carbonylthiochroman |
|  | 4-Methoxy-5,8-dimethyl-6-(5-hydroxy-1,3-dimethylpyrazol-4-yl)carbonylthiochroman-1,1-dioxide |
|  | 4-Methoxy-5,8-dimethyl-6-(5-p-toluenesulfonyloxy-1,3-dimethylpyrazol-4-yl)-carbonylthiochroman-1,1-dioxide |
|  | 4-Methoxy-3,5,8-trimethyl-6-(1-ethyl-5-hydroxypyrazol-4-yl)carbonylthiochroman-1,1-dioxide |

TABLE 1-continued

| Structural formula | Name |
|---|---|
| (structure) | 4-Methoxy-3,5,8-trimethyl-6-(1-ethyl-5-p-toluene-sulfonyloxypyrazol-4-yl)-carbonylthiochroman-1,1-dioxide |
| (structure) | 4-Methoxy-3,3,5,8-tetra-methyl-6-(1-ethyl-5-hydroxy-pyrazol-4-yl)carbonyl-thiochroman-1,1-dioxide |
| (structure) | 4-Methoxy-2,3,5,8-tetra-methyl-6-(1-ethyl-5-hydroxy-pyrazol-4-yl)carbonyl-thiochroman-1,1-dioxide |
| (structure) | 4-Methoxy-2,2,3,3,5,8-hexamethyl-6-(1-ethyl-5-hydroxypyrazol-4-yl)-carbonylthiochroman-1,1-dioxide |
| (structure) | 3-Ethyl-4-methoxy-5,8-dimethyl-6-(1-ethyl-5-hydroxypyrazol-4-yl)-carbonylthiochroman-1,1-dioxide |
| (structure) | 4-Methoxy-5,8-dimethyl-6-(1-ethyl-5-hydroxypyrazol-4-yl)carbonylthiochroman-1-oxide |
| (structure) | 4-Methoxy-5,8-dimethyl-6-(5-(4-chlorophenyl)sulfonyl-oxy-1-ethylpyrazol-4-yl)-carbonylthiochroman |

TABLE 1-continued

| Structural formula | Name |
|---|---|
| (structure) | 5,8-Dichloro-4-methoxy-3-methyl-6-(1-ethyl-5-hydroxy-pyrazol-4-yl)carbonylthiochroman |
| (structure) | 5,8-Dichloro-4-methoxy-3-methyl-6-(1-ethyl-5-hydroxy-pyrazol-4-yl)carbonyl-thiochroman-1,1-dioxide |
| (structure) | 5,8-Difluoro-4-methoxy-6-(1-ethyl-5-hydroxypyrazol-4-yl)carbonylthiochroman |
| (structure) | 5,8-Difluoro-4-methoxy-6-(1-ethyl-5-hydroxypyrazol-4-yl)carbonylthiochroman-1,1-dioxide |
| (structure) | 5,8-Difluoro-4-ethoxy-6-(1-ethyl-5-hydroxypyrazol-4-yl)carbonylthiochroman |
| (structure) | 5,8-Difluoro-4-ethoxy-6-(1-ethyl-5-hydroxypyrazol-4-yl)carbonylthiochroman-1,1-dioxide |
| (structure) | 5-Chloro-4-methoxy-6-(5-phenylsulfonyloxy-1-ethyl-pyrazol-4-yl)carbonylthiochroman-1,1-dioxide |

TABLE 1-continued

| Structural formula | Name |
|---|---|
| (structure) | 5-Chloro-4-methoxy-6-(1-ethyl-5-p-toluenesulfonyl-oxypyrazol-4-yl)carbonyl-thiochroman-1,1-dioxide |
| (structure) | 5-Chloro-4-methoxy-6-(1-ethyl-5-n-propylsulfonyl-oxypyrazol-4-yl)carbonyl-thiochroman-1,1-dioxide |
| (structure) | 5-Chloro-4-methoxy-6-(1-ethyl-5-i-propylsulfonyl-oxypyrazol-4-yl)carbonyl-thiochroman-1,1-dioxide |
| (structure) | 8-Chloro-4-methoxy-5-methyl-6-(1-ethyl-5-n-propyl-sulfonyloxypyrazol-4-yl)-carbonylthiochroman-1,1-dioxide |
| (structure) | 8-Chloro-4-methoxy-5-methyl-6-(5-phenylsulfonyloxy-1-ethylpyrazol-4-yl)-carbonylthiochroman-1,1-dioxide |

The pyrazole derivative of the general formula (I) contains some asymmetric carbon atoms, and includes a variety of isomers. The pyrazole of the present invention includes all of these isomers and isomer mixtures of these.

The pyrazole derivative of the general formula (I) in which $Q^1$ is hydrogen, i.e., the pyrazole derivative of the formula (Ia) to be described later, can have the following three structures due to its tautomerism. The pyrazole derivative of the present invention includes all of compounds having these structures.

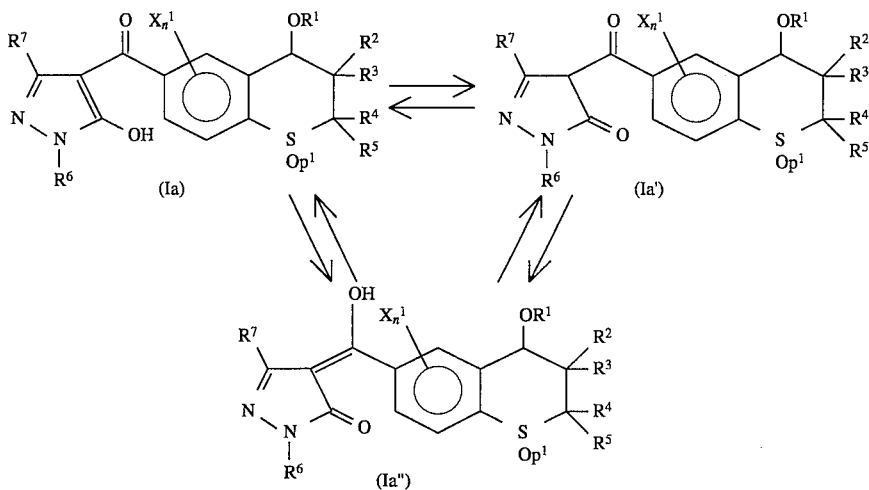

Further, the pyrazole derivative of the general formula (Ia) is an acidic substance, and can be easily converted to a salt by treating it with a base. This salt is also included in the pyrazole derivative of the present invention.

The above base is selected from known bases without any limitation, and examples thereof include organic bases such as amines and anilines and inorganic bases such as sodium salts and potassium salts.

The amines include alkylamine, dialkylamine and trialkylamine. The alkyl group thereof is generally a $C_1$–$C_4$ alkyl group. The anilines include aniline, alkylaniline and dialkylaniline. The alkyl group thereof is generally a $C_1$–$C_4$ alkyl group.

The sodium salts include sodium hydroxide and sodium carbonate. The potassium salts include potassium hydroxide and potassium carbonate.

The pyrazole derivative of the general formula (I) can be produced by any one of three processes provided by the present invention. These processes will be explained one by one hereinafter.

The first process comprises reacting a compound of the general formula (II).

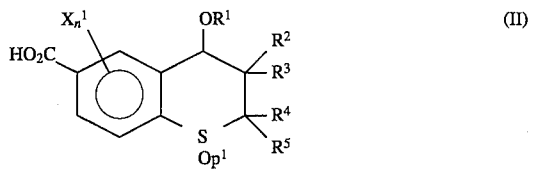

[wherein $R^1$, $R^2$, $R^3$, $R^4$, $R^5$, $X^1$, n and $p^1$ are as defined in the general formula (I)],
with a compound of the general formula (III),

[wherein $R^6$ and $R^7$ are as defined in the general formula (I)], to form a pyrazole derivative of the general formula (Ia),

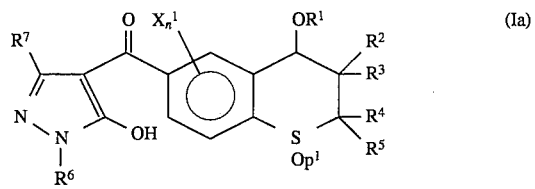

[wherein $R^1$, $R^2$, $R^3$, $R^4$, $R^5$, $R^6$, $R^7$, $X^1$, n and $p^1$ are as defined in the above general formulae (II) and (III)],
and optionally reacting the above pyrazole derivative (Ia) with a sulfonic acid halide of the general formula (IV), $$Q^2 X^2 \qquad (IV)$$

[wherein $Q^2$ is —$SO_2$—$R^8$ or

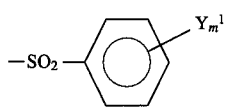

in which $R^8$ is a $C_1$–$C_6$ alkyl group,

Y is hydrogen, a $C_1$–$C_4$ alkyl group or a halogen atom, and $m^1$ is an integer of 1 to 3, and $X^2$ is a halogen atom], to obtain a pyrazole derivative of the general formula (Ib),

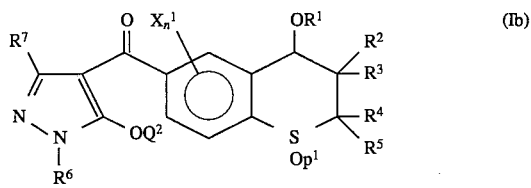

[wherein $R^1$, $R^2$, $R^3$, $R^4$, $R^5$, $R^6$, $R^7$, $X^1$, n, $p^1$ $Q^2$, $R^8$, Y and $m^1$ are as defined in the above general formulae (II), (III) and (IV)].

For making it easier to understand the first process above, the reaction scheme of the first process will be described below.

First Process

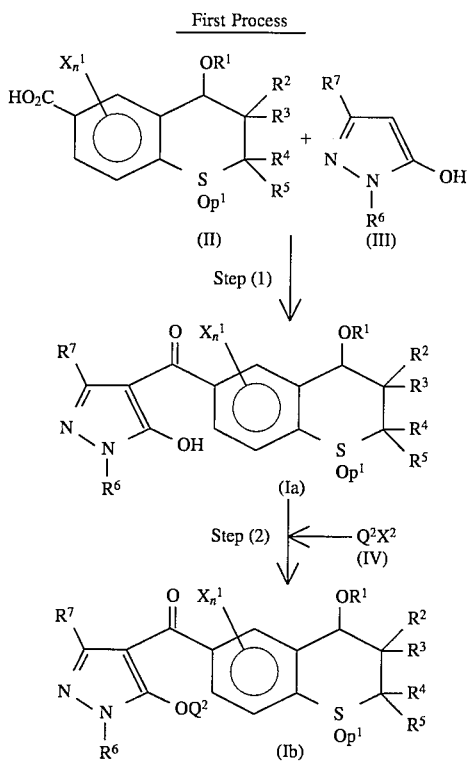

In the step (1), the compound of the general formula (II) and the compound of the general formula (III) are allowed to react, for example, in the presence of N,N'-dicyclohexylcarbodiimide (to be abbreviated as DCC hereinafter) and a base in an inert solvent to obtain a pyrazole derivative of the general formula (Ia). The pyrazole derivative of the general formula (Ia) obtained in the above step is included in the pyrazole derivative of the general formula (I), provided by the present invention, (that is, the pyrazole derivative of the general formula (Ia) corresponds to the pyrazole derivative of the general formula (I) in which $Q^1$ is hydrogen).

In the above step (1), the molar ratio of the compound of the general formula (II) to the compound of the general formula (III) is preferably 1:1 to 1:3. DCC is used in an amount of 1.0 to 1.5 mol per mole of the compound of the general formula (II) and the compound of the general formula (III). The base used together with DCC is not specially limited, while it is preferred to use potassium carbonate or sodium carbonate in an amount of 0.5 to 2.0 mol per mole of the compound of the general formula (II) and the compound of the general formula (III). The inert solvent is not specially limited, either, if it is inert to the reaction. However, it is preferably selected from tert-butyl alcohol, tert-amyl alcohol and i-propyl alcohol. The reaction temperature may be from room temperature to the boiling point of the solvent, while it is preferably from approximately 50° to 100° C.

In the step (2), the pyrazole derivative of the general formula (Ia) obtained in the step (1) and the sulfonic acid halide of the general formula (IV) are allowed to react in an inert solvent to obtain a pyrazole derivative of the general formula (Ib). The pyrazole derivative of the general formula (Ib) obtained in this step (2) is also included in the pyrazole derivative of the general formula (I) (that is, the pyrazole derivative of the general formula (Ib) corresponds to the pyrazole derivative of the general formula (I) in which $Q^1$ is —$SO_2$—$R^8$ or

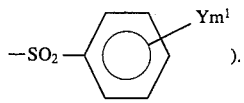

In the above step (2), the molar ratio of the compound of the general formula (Ia) to the compound of the general formula (IV) is preferably 1:1 to 1:10. The inert solvent is not specially limited if it is inert to the reaction, while it is preferably selected, for example, from ethers such as diethyl ether and tetrahydrofuran and halogenated hydrocarbons such as dichloromethane and chloroform. In the above step (2), the reaction is preferably carried out in the presence of a base such as sodium carbonate, potassium carbonate, triethylamine or pyridine generally at a temperature of from room temperature to the boiling point of the solvent, Further, the reaction may be carried out in a two-phase solvent system such as water-benzene, water-toluene, water-chloroform or water-dichloromethane. In this case, the reaction proceeds more smoothly when a phase transfer catalyst such as crown ether or benzyltriethylammonium chloride is added to the reaction system.

The pyrazole derivative of the general formula (I) can be also produced by a second process to be detailed below.

The second process comprises reacting a compound of the general formula (II).

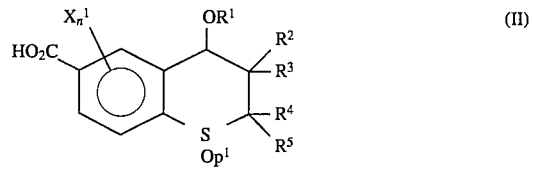

[wherein $R^1$, $R^2$, $R^3$, $R^4$, $R^5$, $X^1$, n and $p^1$ are as defined in the general formula (I)].

with a halogenation agent to form a compound of the general formula (V),

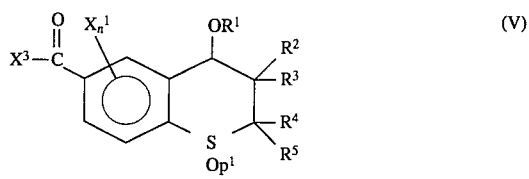

[wherein $R^1$, $R^2$, $R^3$, $R^4$, $R^5$, $X^1$, n and $p^1$ are as defined in the general formula (I) and $X^3$ is a halogen atom], then reacting the above compound (V) with a compound of the general formula (III).

[wherein $R^6$ and $R^7$ are as defined in the general formula (I)]

to form a compound of the general formula (VI),

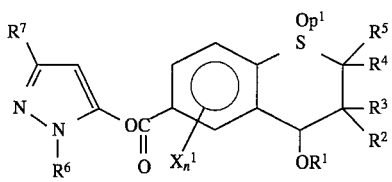

[wherein $R^1$, $R^2$, $R^3$, $R^4$, $R^5$, $R^6$, $R^7$, $X^1$, n and $p^1$ are as defined in the general formula (I)], then heating the above compound (VI) to form a pyrazole derivative of the general formula (Ia),

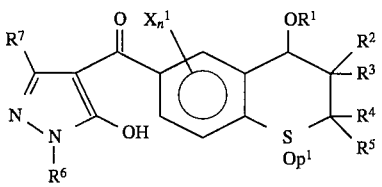

[wherein $R^1$, $R^2$, $R^3$, $R^4$, $R^5$, $R^6$, $R^7$, $X^1$, n and $p^1$ are as defined in the general formula (I)], and optionally reacting the above pyrazole derivative (Ia) with a sulfonic acid halide of the general formula (IV), $$Q^2X^2 \quad \text{(IV)}$$

[wherein $Q^2$ is $-SO_2-R^8$ or

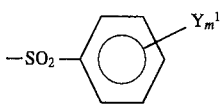

in which $R^8$ is a $C_1$–$C_6$ alkyl group,

Y is hydrogen, a $C_1$–$C_4$ alkyl group or a halogen atom, and $m^1$ is an integer of 1 to 3, and $X^2$ is a halogen atom], to obtain a pyrazole derivative of the general formula (Ib),

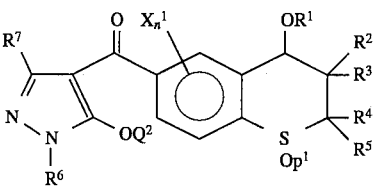

[wherein $R^1$, $R^2$, $R^3$, $R^4$, $R^5$, $R^6$, $R^7$, $X^1$, n, $p^1$, $Q^2$, $R^8$, Y and $m^1$ are as defined in the above general formulae (II), (III) and (IV)].

For making it easier to understand the second process above, the reaction scheme of the second process will be described below.

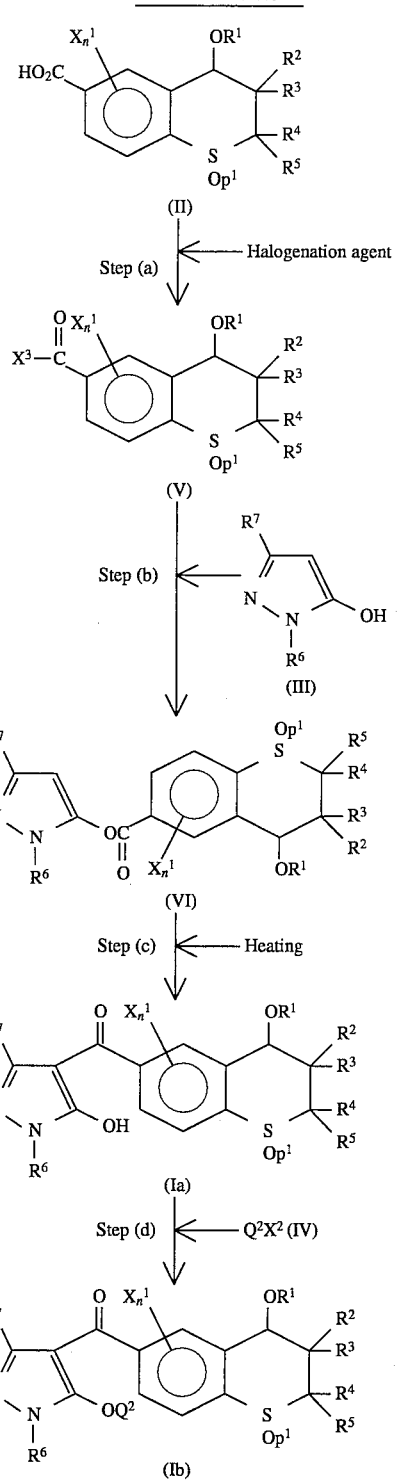

In the step (a), the compound of the general formula (II) is allowed to react with a halogenation agent (thionyl chloride or phosphorus oxychloride) to form a compound of the general formula (V). The above step (a) is preferably carried out in the presence of a halogenation agent in an amount greater than the equimolar amount of the compound of the general formula (II). This reaction may be carried out in a diluted state in the presence of an inert solvent (methylene chloride or chloroform), or may be carried out in the absence of a solvent. Further, the reaction may be carried out using, as a solvent, an excess amount of thionyl chloride which is a halogenation agent. Although not specially limited, the reaction temperature is preferably from 0° C. to the boiling point of the solvent, particularly preferably 60° C. or around 60° C.

In the step (b), the compound of the general formula (V) obtained in the step (a) is allowed to react with the compound of the general formula (III) to form the compound of the general formula (VI). The step (b) is preferably carried out with a molar ratio of the compound of the general formula (V) to the compound of the general formula (III) at 1:1 to 1:3 in a solvent inert to the reaction such as dioxane, acetonitrile, benzene, toluene, chloroform, methylene chloride or 1,2-dichloroethane. Further, the reaction may be carried out in a two-phase solvent system such as water-benzene, water-toluene, water-chloroform or water-dichloromethane. The reaction smoothly proceeds in the co-presence of a base such as sodium hydroxide, potassium hydroxide, sodium carbonate, potassium carbonate, triethylamine or pyridine. The reaction temperature is preferably between 0° C. and 60° C., generally room temperature.

In the step (c), the compound of the general formula (VI) obtained in the step (b) is heated to obtain the pyrazole derivative of the general formula (Ia). The pyrazole derivative of the general formula (Ia) obtained in this step (c) is included in the pyrazole derivative of the general formula (I) (that is, the pyrazole derivative of the general formula (Ia) corresponds to the pyrazole derivative of the general formula (I) in which $Q^1$ is hydrogen).

In the step (c), it is preferred to heat the compound of the general formula (VI) in the presence of a proper base (sodium carbonate, potassium carbonate or triethylamine). The amount of the base is at least an equimolar amount to the compound of the general formula (VI), while it is generally preferably 1.5 mol per mole of the compound of the general formula (VI). The heating temperature is preferably 80° to 150° C. A solvent is not particularly required, while a solvent (dioxane or acetonitrile) inert to the reaction may be used.

The step (d) is the same as the step (2) in the first process described already. In the step (d), the pyrazole derivative of the general formula (Ia) obtained in the step (c) and the sulfonic acid halide of the general formula (IV) are allowed to react in an inert solvent to obtain the pyrazole derivative of the general formula (Ib). The pyrazole derivative of the general formula (Ib) obtained in this step (d) is also included in the pyrazole derivative of the general formula (I) (that is, the pyrazole derivative of the general formula (Ib) corresponds to the pyrazole derivative of the general formula (I) in which $Q^1$ is —$SO_2$—$R^8$ or

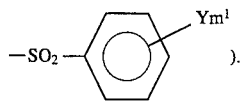

In the above step (d), the molar ratio of the compound of the general formula (Ia) to the compound of the general formula (IV) is preferably 1:1 to 1:10. The inert solvent is not specially limited if it is inert to the reaction. However, the inert solvent is preferably selected, for example, from ethers such as diethyl ether and tetrahydrofuran and halogenated hydrocarbons such as dichloromethane and chloroform. The step (d) is preferably carried out in the presence of a base such as sodium carbonate, potassium carbonate, triethylamine or pyridine generally at a temperature of from room temperature to the boiling point of the solvent. Further, the reaction may be carried out in a two-phase solvent system such as water-benzene, water-toluene, water-chloroform or water-dichloromethane. In this case, the reaction proceeds more smoothly when a phase transfer catalyst such as crown ether or benzyltriethylammonium chloride is added to the reaction system.

The pyrazole derivative of the general formula (I) in which $p^1$ is 1 (sulfoxide) or 2 (sulfone), i.e., a pyrazole derivative of the general formula (Ic).

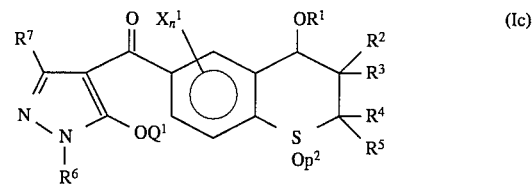

[wherein $p^2$ is 1 or 2, $R^1$, $R^2$, $R^3$, $R^4$, $R^5$, $R^6$, $R^7$, $X^1$, n, $Q^1$, $R^8$, Y and $m^1$ are as defined in the above general formula (I)]

can be also produced by the following third process.

The third process comprises oxidizing the sulfur atom of the pyrazole derivative of the general formula (I) in which $p^1$ is 0 (sulfide), provided by the present invention, i.e., a compound of the general formula (Id),

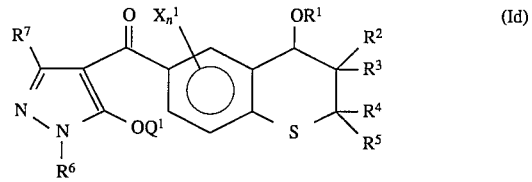

[wherein $R^1$, $R^2$, $R^3$, $R^4$, $R^5$, $R^6$, $R^7$, $X^1$, n, $Q^1$, $R^8$, Y and $m^1$ are as defined the above general formula (I)], with a proper oxidizing agent to obtain the pyrazole derivative of the general formula (Ic).

The above oxidizing agent can be selected from a variety of compounds, while it is preferably selected from hydrogen peroxide, peracetic acid and sodium metaperiodate. Hydrogen peroxide is particularly preferred.

The solvent which is to be used is not specially limited if it is inert to the reaction, while acetic acid is preferred.

The reaction temperature is preferably in the range of from room temperature to the boiling point of the solvent.

For producing the pyrazole derivative of the general formula (Ic) in which $p^2$ is 1 (sulfoxide), provided by the present invention, i.e., a pyrazole derivative of the general formula (Ie),

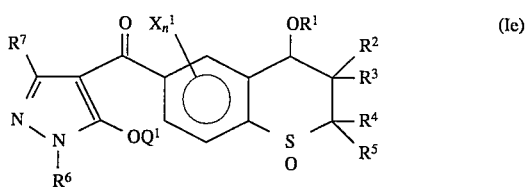

[wherein $R^1$, $R^2$, $R^3$, $R^4$, $R^5$, $R^6$, $R^7$, $X^1$, n, $Q^1$, $R^8$, Y and $m^1$ are as defined in the above general formula (I)], the reaction is preferably carried out in the presence of the oxidizing agent in an amount of 1 equivalent around room temperature.

For producing the pyrazole derivative of the general formula (Ic) in which $p^2$ is 2 (sulfone), provided by the present invention, i.e., a pyrazole derivative of the general formula (If),

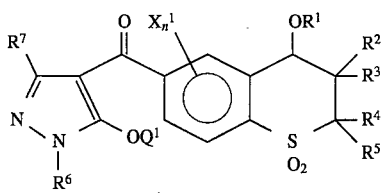

[wherein $R^1$, $R^2$, $R^3$, $R^4$, $R^5$, $R^6$, $R^7$, $X^1$, n, $Q^1$, $R^8$, Y and $m^1$ are as defined in the above general formula (I)], the reaction is preferably carried out in the presence of the oxidizing agent in an amount of at least 2 equivalents at 50° to 100° C.

The compound of the general formula (II) used as the starting material in each of the above first and second processes for the production of the pyrazole derivative of the general formula (I) is a novel intermediate compound, and can be synthesized by various methods. For example, it can be synthesized according to the following reaction scheme.

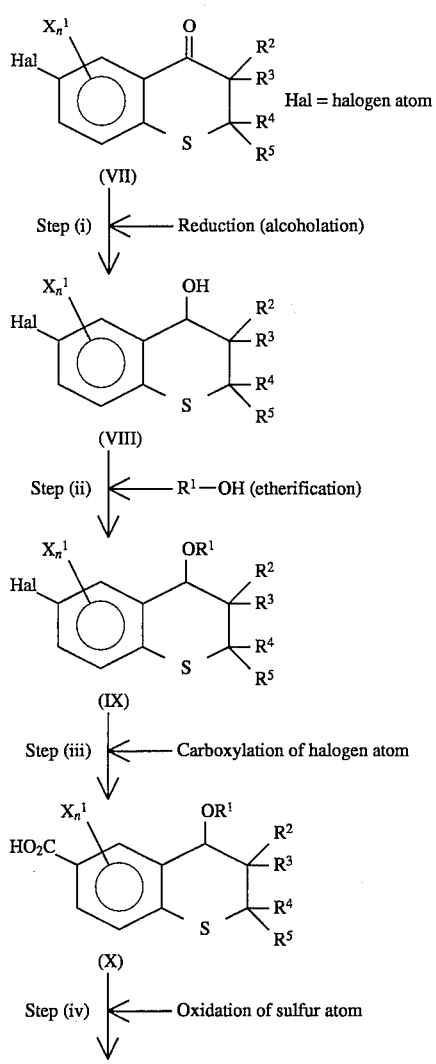

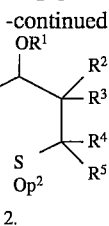

$p^2$ is 1 or 2.

The steps (i), (ii), (iii) and (iv) will be explained hereinafter.

In the step (i), the thiochroman-4-one of the general formula (VII) is reduced to form an alcohol of the general formula (VIII). The reaction temperature is generally −20° C. to 50° C. The reducing agent is selected from a variety of compounds, and sodium borohydride is used for example. The thiochroman-4-one of the general formula (VII) used as a starting material can be produced by a variety of methods, such as the methods described in JP-A-58-198483, International Publication WO 88/08155, and Canadian Journal of Chemistry, vol. 51, page 839 (1973).

In the step (ii), the alcohol of the general formula (VIII) and the alcohol of the general formula. $R^1OH$. are allowed to undergo dehydrative condensation to form an ether of the general formula (IX). The solvent is selected from aromatic hydrocarbon solvents such as benzene, toluene and xylene and halogenated hydrocarbon solvents such as 1,2-dichloroethane and carbon tetrachloride. An excess of the alcohol of $R^1OH$ may be used as a solvent. The catalyst is selected from acid catalysts such as sulfuric acid, aromatic sulfonic acid, aromatic sulfonic acid halide, boron trifluoride and aluminum chloride, whereby the reaction proceeds smoothly. The temperature is generally 80° C. to the boiling point of the solvent, and it is preferably the reflux temperature of the alcohol of $R^1OH$.

In the step (iii), the compound of the general formula (IX) and magnesium are allowed to react to form a Grignard reagent, and carbon dioxide is allowed to react with the Grignard reagent to form a carboxylic acid of the general formula (X). The reaction temperature is generally 0° to 50° C. The solvent to be used is preferably selected from diethyl ether and tetrahydrofuran. The compound of the general formula (X) corresponds to the compound of the general formula (II) in which $p^1$ is 0 (sulfide).

In the step (iv), the sulfur atom of the carboxylic acid of the general formula (X) is oxidized to form a compound of the general formula (XI), in which the compound of the general formula (XI) corresponds to compounds of the general formula (II) in which $p^1$ is 1 (sulfoxide) and $p^1$ is 2 (sulfone). The reaction temperature is generally room temperature to 100° C. The oxidizing agent is selected from a variety of compounds, and hydrogen peroxide is particularly preferred. The solvent is selected from a variety of solvents, and acetic acid is particularly preferred. For producing the compound (sulfoxide) in which $p^1$ is 1, the reaction is carried out in the presence of 1 equivalent of the oxidizing agent at room temperature. For producing the compound (sulfone) in which $p^1$ is 2, the reaction is carried out in the presence of at least 2 equivalents at 0° to 100° C.

The compound of the general formula (XII),

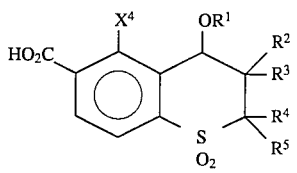

[wherein $X^4$ is a $C_1$–$C_4$ alkyl group, and $R^1$, $R^2$, $R^3$, $R^4$ and $R^5$ are as defined in the above general formula (I)], which is included in the compound of the general formula (II), can be synthesized by the above reaction scheme, while it can be also synthesized by treating the compound of the general formula (XIII) obtained by the above reaction scheme,

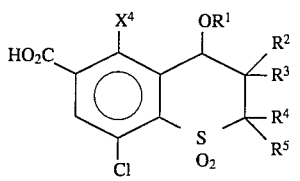

[wherein $X^4$ is a $C_1$–$C_4$ alkyl group, and $R^1$, $R^2$, $R^3$, $R^4$ and $R^5$ are as defined in the above general formula (I)], with a proper reducing agent.

The proper reducing agent is selected from a variety of compounds, while zinc is preferred. The solvent is preferably selected from water and alcohol solvents such as ethanol and a mixture of these. The reaction is carried out at a temperature in the range of room temperature to the boiling point of the solvent, preferably 80° to 100° C. Further, the reaction proceeds smoothly when a strong base such as sodium hydroxide or potassium hydroxide is added.

The compound of the general formula (II) obtained as described above is a novel compound, and can be used as a starting material for the production of the pyrazole derivative of the general formula (I).

The pyrazole compound of the general formula (III) used as a reaction agent in each of the above first and second processes can be synthesized, for example, by the method described in JP-A-61-257974.

The herbicide of the present invention contains the novel pyrazole derivative or the salt thereof, provided by the present invention, as an active ingredient, and used as follows. The pyrazole derivative or the salt thereof is mixed with a liquid cattier such as a solvent or a solid carrier such as a fine mineral powder, and the mixture is prepared into the form of a wettable powder, an emulsion, a dust or granules. For imparting these compounds with emulsifiability, dispersibility and wettability in producing the above preparations, a surfactant can be added.

When the herbicide of the present invention is used in the form of a wettable powder, a composition is prepared by mixing 10 to 55% by weight of the pyrazole derivative or the salt thereof, provided by the present invention, 40 to 88% by weight of a solid carrier and 2 to 5% by weight of a surfactant, and the resultant composition may be used. When it is used in the form of an emulsion, the emulsion can be prepared by mixing 20 to 50% by weight of the pyrazole derivative or the salt thereof, provided by the present invention, 35 to 75% by weight of a solvent and 5 to 15% by weight of a surfactant.

On the other hand, when the herbicide of the present invention is used in the form of dust, generally, the dust can be prepared by mixing 1 to 15% by weight of the pyrazole derivative or the salt thereof, provided by the present invention, 80 to 97% by weight of a solid carrier and 2 to 5% by weight of a surfactant. Further, when it is used in the form of granules, the granules can be prepared by mixing 1 to 15% by weight of the pyrazole derivative or the salt thereof, provided by the present invention, 80 to 97% by weight of a solid carrier and 2 to 5% by weight of a surfactant. This solid carrier is selected from fine mineral powders, and examples of these fine mineral powders include diatomaceous earth, oxides such as slaked lime, phosphates such as apatite, sulfates such as gypsum, and silicates such as talc, pyrophyllite, clay, kaolin, bentonite, acid clay, white carbon, powdered quartz and a silica powder.

The above solvent is selected from organic solvents, and specific examples of the organic solvents include aromatic hydrocarbons such as benzene, toluene and xylene, chlorinated hydrocarbons such as o-chlorotoluene, trichloromethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, dimethyl ether and methyl ethyl ether, esters such as isopropyl acetate, benzyl acetate and methyl phthalate, amides such as dimethylformamide, and mixtures of these.

Further, the above surfactant is selected from anionic surfactants, nonionic surfactants, cationic surfactants and amphoteric surfactants (amino acid and betaine).

The herbicide of the present invention may contain other herbicidally active component as an optional active ingredient in combination with the pyrazole derivative of the formula (I) or the salt thereof. This "other" herbicidally active component includes known herbicides such as phenoxy, diphenylether, triazine, urea, carbamate, thiolcarbamate, acid anilide, pyrazole,, phosphoric acid, sulfonylurea and oxadiazon herbicides. This "other" herbicide is properly selected from these herbicides.

Further, the herbicide of the present invention may be used in combination with an insecticide, a fungicide, a plant growth regulator and a fertilizer as required.

EXAMPLES

The present invention will be further explained hereinafter with reference to Examples. However, the present invention shall not be limited to these Examples.

Preparation Example 1

A) 4.4 Grams (0.017 mol) of 6-bromo-5-methylthiochroman-4-one was dissolved in 10 ml of methylene chloride and 10 ml of methanol. The solution was cooled to 0° C. with a salt water-ice bath. 0.32 Grams (0.0085 mol) of sodium borohydride was gradually added so that the temperature did not exceed 10° C. While the mixture was cooled with the ice bath, it was allowed to react for 1 hour. Then, the reaction mixture was poured into 100 ml of 5% hydrochloric acid, and extracted with methylene chloride. The methylene chloride layer was dried over anhydrous sodium sulfate, and the solvent was distilled off under reduced pressure. Added to the resultant oil were 20 ml of methanol and 0.3 g of concentrated sulfuric acid, and the mixture was refluxed under heat for 2 hours. The reaction mixture was allowed to cool, poured into 200 ml of water and extracted with methylene chloride. The methylene chloride layer was dried over anhydrous sodium sulfate, and the solvent was distilled off under reduced pressure to give 4.3 g of 6-bromo-4-methoxy-5-methylthiochroman as oil.

B) 1.75 Grams (0.021 mol) of magnesium was placed in a 500-ml three-necked flask, and 100 ml of dry tetrahydrofuran was added to suspend the magnesium therein. Then, 4.3 g (0.016 mol) of 6-bromo-4-methoxy-5-methylthiochroman obtained in A) and 3.5 g (0.032 mol) of ethyl bromide were added, and the mixture was refluxed under heat for 3 hours. The reaction mixture was allowed to cool, and then cooled with an ice bath. When the internal temperature was decreased to 10° C., carbon dioxide gas was bubbled. After the bubbling was carried out for 30 minutes, the reaction mixture was again cooled with the ice bath, and when the temperature was 10° C., 200 ml of 5% hydrochloric acid was added to remove an excess of magnesium. The reaction mixture was extracted with ethyl acetate. The ethyl acetate layer was extracted with 100 ml of a 5% potassium carbonate aqueous solution three times. To the resultant potassium carbonate solution was added 10% hydrochloric acid to adjust the pH to 1. A precipitated solid was recovered by filtration, and dried to give 2.9 g (0.012 mol) of 4-methoxy-5-methylthiochroman-6-carboxylic acid (Compound 1). The yield from the 6-bromo-5-methylthiochroman-4-one was 71%.

Preparation Examples 2–10

Compounds 2–10 shown in Table 2, right column, were obtained in the same manner as in Example 1 except that the 6-bromo-5-methylthiochroman-4-one as the starting material was replaced with compounds shown in Table 2, left column.

Preparation Examples 11–14

Compounds 11–14 shown in Table 2, right column, were obtained in the same manner as in Example 1 except that the 6-bromo-5-methylthiochroman-4-one as the starting material was replaced with compounds shown in Table 2, left column and that the methanol in Preparation Example 1 was replaced with ethanol.

Preparation Example 15

8-Chloro-4-n-propoxy-5-methylthiochroman-6-carboxylic acid (Compound 15) shown in Table 2 was obtained in the same manner as in Example 1 except that the 6-bromo-5-methylthiochroman-4-one in Example 1 was replaced with 6-bromo-8-chloro-5-methylthiochroman-4-one and that the methanol was replaced with n-propanol.

Preparation Example 16

8-Chloro-4-i-propoxy-5-methylthiochroman-6-carboxylic acid (Compound 16) shown in Table 2 was obtained in the same manner as in Example 1 except that the 6-bromo-5-methylthiochroman-4-one in Example 1 was replaced with 6-bromo-8-chloro-5-methylthiochroman-4-one and that the methanol was replaced with i-propanol.

Preparation Example 17

5,8-Dimethyl-4-n-butoxythiochroman-6-carboxylic acid (Compound 17) shown in Table 2 was obtained in the same manner as in Example 1 except that the 6-bromo-5-methylthiochroman-4-one in Example 1 was replaced with 6-bromo-5,8-dimethylthiochroman-4-one and that the methanol was replaced with n-butanol.

Preparation Example 18

A 50-ml egg-plant type flask was charged with 4.8 g (0.02 mol) of 4-methoxy-5-methylthiochroman-6-carboxylic acid, 20 ml of acetic acid and 6.8 g (0.06 mol) of a 30% hydrogen peroxide aqueous solution, and the mixture was heated at 100° C. for 1 hour. After allowed to cool, the reaction mixture was poured into 100 ml of water. The precipitated oil was extracted with ethyl acetate, and the extract was dried over anhydrous sodium sulfate and concentrated under reduced pressure to give 4.6 g of 4-methoxy-5-methylthiochroman-6-carboxylic acid-1,1-dioxide (Compound 18) shown in Table 2.

Preparation Examples 19–30

Compounds 19 to 30 shown in Table 2, right column, were obtained in the same manner as in Preparation Example 18 except that the 4-methoxy-5-methylthiochroman-6-carboxylic acid used as the starting material in Preparation Example 18 was replaced with starting materials shown in Table 2, left column.

Preparation Example 31

A 50-ml egg-plant type flask was charged with 2.9 g (0.011 mol) of 4-ethoxy-5,8-dimethylthiochroman-6-carboxylic acid, 10 ml of acetic acid and 1.3 g (0.011 mol) of a 30% hydrogen peroxide aqueous solution, and the mixture was allowed to react at room temperature for 12 hours. Then, the reaction mixture was poured into 100 ml of water. The precipitated oil was extracted with ethyl acetate, and the extract was dried over anhydrous sodium sulfate and concentrated under reduced pressure to give 2.5 g of 4-ethoxy-5,8-dimethylthiochroman-6-carboxylic acid-1-oxide (Compound 31) shown in Table 2.

Preparation Example 32

A 50-ml egg-plant type flask was charged with 1.36 g (0.0041 mol) of 8-chloro-4-n-propoxy-5-methylthiochroman-6-carboxylic acid-1,1-dioxide, 1.35 g (0.02 mol) of potassium hydroxide, 0.81 g (0.012 mol) of a zinc powder, 10 ml of water and 6 ml of ethanol, and the mixture was refluxed under heat for 10 hours. After allowed to cool, insolubles were removed by filtration, and the ethanol was distilled off under reduced pressure. Then, while the remainder was cooled with ice, 50 ml of 5% hydrochloric acid was added to adjust the pH to 1. The reaction mixture was extracted with ethyl acetate. The ethyl acetate layer was washed with 2% hydrochloric acid, washed with a saturated sodium chloride aqueous solution, and dried over anhydrous sodium sulfate. The solvent was removed under reduced pressure to give 1.0 g of 4-n-propoxy-5-methylthiochroman-6-carboxylic acid-1,1-dioxide (Compound 32) shown in Table 2.

Preparation Example 33

1.1 Grams of 4-i-propoxy-5-methylthiochroman-6-carboxylic acid-1,1-dioxide (Compound 33) shown in Table 2 was obtained in the same manner as in Example 32 except that the 8-chloro-4-n-Propoxy-5-methylthiochroman-6-carboxylic acid-1,1-dioxide in Preparation Example 32 was replaced with 8-chloro-4-i-propoxy-5-methylthiochroman-6-carboxylic acid-1,1-dioxide.

Table 2 shows the structures and yields of Compounds 1 to 33 obtained in the above Examples 1 to 33, and Table 3 shows the physical properties thereof.

TABLE 2

| Prep. Ex. No. | Starting material | Prepared Compd No. | Structural formula | Yield (%) |
|---|---|---|---|---|
| 1 | [structure] | 1 | [structure] | 71 |
| 2 | [structure] | 2 | [structure] | 30 |
| 3 | [structure] | 3 | [structure] | 22 |
| 4 | [structure] | 4 | [structure] | 52 |
| 5 | [structure] | 5 | [structure] | 74 |
| 6 | [structure] | 6 | [structure] | 19 |
| 7 | [structure] | 7 | [structure] | 70 |
| 8 | [structure] | 8 | [structure] | 38 |

TABLE 2-continued

| Prep. Ex. No. | Starting material | Prepared Compd No. | Structural formula | Yield (%) |
|---|---|---|---|---|
| 9 | (structure) | 9 | (structure) | 77 |
| 10 | (structure) | 10 | (structure) | 32 |
| 11 | (structure) | 11 | (structure) | 60 |
| 12 | (structure) | 12 | (structure) | 83 |
| 13 | (structure) | 13 | (structure) | 87 |
| 14 | (structure) | 14 | (structure) | 54 |
| 15 | (structure) | 15 | (structure) | 71 |
| 16 | (structure) | 16 | (structure) | 51 |
| 17 | (structure) | 17 | (structure) | 71 |

TABLE 2-continued

| Prep. Ex. No. | Starting material | Prepared Compd No. | Structural formula | Yield (%) |
|---|---|---|---|---|
| 18 | | 18 | | 85 |
| 19 | | 19 | | 74 |
| 20 | | 20 | | 68 |
| 21 | | 21 | | 89 |
| 22 | | 22 | | 91 |
| 23 | | 23 | | 73 |
| 24 | | 24 | | 90 |
| 25 | | 25 | | 95 |

TABLE 2-continued

| Prep. Ex. No. | Starting material | Prepared Compd No. | Structural formula | Yield (%) |
|---|---|---|---|---|
| 26 | (structure: benzene with $HO_2C$, two $CH_3$, $O$-n-$C_4H_9$, S-ring) | 26 | (structure: same with $SO_2$) | 87 |
| 27 | (structure: benzene with $HO_2C$, two $CH_3$, $OCH_3$, $CH_3$, S-ring) | 27 | (structure: same with $SO_2$) | 91 |
| 28 | (structure: benzene with $HO_2C$, two $CH_3$, $OCH_3$, S-ring) | 28 | (structure: same with $SO_2$) | 100 |
| 29 | (structure: benzene with $HO_2C$, $CH_3$, $O$-n-$C_3H_7$, Cl, S-ring) | 29 | (structure: same with $SO_2$) | 93 |
| 30 | (structure: benzene with $HO_2C$, $CH_3$, $O$-i-$C_3H_7$, Cl, S-ring) | 30 | (structure: same with $SO_2$) | 97 |
| 31 | (structure: benzene with $HO_2C$, two $CH_3$, $OC_2H_5$, S-ring) | 31 | (structure: same with $SO$) | 81 |
| 32 | (structure: benzene with $HO_2C$, $CH_3$, $O$-n-$C_3H_7$, Cl, $SO_2$-ring) | 32 | (structure: same with $SO_2$) | 83 |
| 33 | (structure: benzene with $HO_2C$, $CH_3$, $O$-i-$C_3H_7$, Cl, $SO_2$-ring) | 33 | (structure: same with $SO_2$) | 93 |

TABLE 3

| Compd No. | Infrared absorption spectrum *1 (cm$^{-1}$) | Proton nuclear magnetic resonance spectrum (ppm) |
|---|---|---|
| 1 | 1700(C=O) 2880, 2960, 3000(C—H) 2550~3450(O—H) | 1.55~1.95(H, m)2.45~2.95(2H, m) 2.65(3H, s)3.10~3.36(H, m) 3.46(3H, s)4.53~4.63(H, m) 7.05(H, d)7.78(H, d) *2 |
| 2 | 1695(C=O) 2830, 3000(C—H) 2550~3450(O—H) | 1.52~1.93(H, m)2.50~2.90(2H, m) 2.60(3H, s)3.03~3.35(H, m) 3.48(3H, s)4.50~4.60(H, m) 7.56(H, d) *2 |
| 3 | 1695(C=O) 2950, 3000(C—H) 2550~3450(O—H) | 1.50~1.90(H, m)2.55~3.00(2H, m) 3.14~3.44(H, m)3.50(3H, s) 4.85~4.98(H, m)7.93(H, s) *2 |
| 4 | 1695(C=O) 2820, 2880, 2930, 2980(C—H) 2550~3450(O—H) | 1.43~1.60(3H, m)2.10~2.85(2H, m) 2.70(3H, s)3.20~3.30(H, m) 3.46(3H, s)4.54~4.75(H, m) 7.56(H, d) *2 |
| 5 | 1695(C=O) 2830, 2940, 3000(C—H) 2550~3450(O—H) | 1.46~1.87(H, m)2.60(3H, s) 2.70~3.05(2H, m)3.15~3.37(H, m) 3.45(3H, s)4.60~4.70(H, m) 7.80(H, s) *3 |
| 6 | 1710(C=O) 2850, 2950, 2990(C—H) 2550~3450(O—H) | 0.88(3H, d)2.55~2.85(2H, m) 3.10~3.35(H, m) 3.47(3H, s)4.60~4.70(H, m) 7.90(H, s)9.75(H, s, broad) *2 |
| 7 | 1700(C=O) 2960, 3000(C—H) 2500~3500(O—H) | 1.50~1.93(H, m)2.25 (3H, s) 2.50~2.90(2H, m)2.63 (3H, s) 3.10~3.30(H, m)3.46(3H, s) 4.56~4.66(H, m)7.72(H, s) *2 |
| 8 | 1700(C=O) 2850, 2950, 3000(C—H) 2500~3450(O—H) | 1.43~1.90(H, m)2.46~3.00(2H, m) 3.13~3.37(H, m)3.46(3H, m) 4.65~4.82(H, m)7.46~7.72(H, m) 9.3(H, s, broad) *2 |
| 9 | 1710(C=O) 2850, 3000(C—H) 2550~3450(O—H) | 0.92(3H, d)2.28(3H, s) 2.54~2.76(2H, m)2.62(3H, s) 3.33~3.60(H, m)3.45(3H, s) 4.25~4.35(H, m)7.72(H, s) *2 |
| 10 | 1730(C=O) 2950(C—H) 2650~3450(O—H) | 1.54~1.95(H, m)2.30(3H, s) 2.39(3H, s)2.55~2.80(2H, m) 3.08~3.30(H, m)3.44(3H, s) 4.40~4.50(H, m)6.87(H, s) 7.10(H, s broad) *2 |
| 11 | 1695(C=O) 2870, 2940, 2980(C—H) 2550~3450(O—H) | 1.27(3H, t)1.43(3H, d) 2.50~2.85(2H, m)2.64(3H, s) 3.35~3.72(H, m)3.78(2H, q) 4.62~4.72(H, m)7.60(H, d) *2 |
| 12 | 1695(C=O) 2940, 3000(C—H) 2550~3450(O=H) | 1.20(3H, t)2.30~3.10(2H, m) 2.61((3H, s)3.20~3.70(2H, m) 3.66~3.90(2H, m)4.77~4.84(H, m) 7.77(H, d)7.98(H, d) 9.5(H, s, broad) *3 |
| 13 | 1695(C=O) 2880, 2940, 2980(C—H) 2550~3450(O—H) | 1.25(3H, t)1.50~1.95(H, m) 2.25(3H, s)2.62(3H, s) 2.50~2.90(2H, m) 3.10~3.37(H, m)3.75(2H, q) 4.63~4.75(H, m)7.70(H, s) *2 |
| 14 | 1670(C=O) 2930, 2970(C—H) 2500~3200(O—H) | 1.22(3H, t)1.50~1.90(H, a) 2.40~3.0(H, m)3.20~3.50(H, m) 3.50~3.90(2H, m)4.80~4.95(H, m) 7.60(H, t)9.8(H, s, broad) *2 |
| 15 | 1695(C=O) 2880, 2950, 2990(C—H) 2550~3450(O—H) | 0.93(3H, t)1.40~1.95(3H, m) 2.65(3H, s)2.30~3.0(2H, m) 3.20~3.85(3H, m)4.80~4.95(H, m) 7.80(H, s) *2 |
| 16 | 1700(C=O) 2900, 2950, 2990(C—H) 2550~3450(O—H) | 1.23(6H, dd)1.46~1.86(H, m) 2.65(3H, s)2.70~3.00(2H, m) 3.13~3.45(H, m)3.84~4.20(H, m) 4.95~5.05(H, m)7.80(H, s) *3 |
| 17 | 1680(C=O) 2860, 2930, 2960(C—H) 2550~3450(O—H) | 0.91(H, t)1.20~1.92(5H, m) 2.25(3H, s)2.62(3H, s) 2.50~2.90(2H, m)3.10~3.35(H, m) 3.65~3.85(2H, m)4.60~4.70(H, m) 7.70(H, s) *2 |
| 18 | 1730(C=O) 2890, 3000(C—H) 2550~3450(O—H) 1130, 1280(SO$_2$) | 2.40~2.75(2H, m) 2.60(3H, s)2.80~3.70(2H, m) 3.50(3H, s)4.70~4.80(H, m) 7.76(H, d)7.97(H, d) *3 |
| 19 | — | 2.30~2.90(2H, m)2.50(3H, s) 3.15~3.90(2H, m)3.51(3H, s) 4.45~4.55(H, m)7.70(H, d) *2 |
| 20 | — | 2.40~2.95(2H, m)3.20~3.85(2H, m) 3.50(3H, s)4.55~4.60(H, m) 7.60(H, s) *2 |
| 21 | — | 1.58(3H, t)2.50~2.70(2H, m) 2.54(3H, s)3.42(H, m)3.49(3H, s) 4.46~4.60(H, m)7.65(H, d) 9.8(H, s, broad) *2 |
| 22 | 1700(C=O) 2840, 2960, 3000(C—H) 2550~3500(O—H) 1140, 1300(SO$_2$) | 2.23~2.50(H, m)2.58(3H, s) 2.77~3.07(H, m)3.20~3.90(2H, m) 3.51(3H. s)4.70~4.77(H, m) 7.89(H, s) *3 |
| 23 | 1730(C=O) 2880, 2940(C—H) 2550~3500(O—H) 1140, 1300(SO$_2$) | 1.20(3H, t)2.30~3.10(2H, m) 2.61(3H, s)3.20~3.70(2H, m) 3.66~3.90(2H, m) 4.77~4.84(H, m)7.77(H, d) 7.98(H, d)9.5(H, s, broad) *3 |
| 24 | 1730(C=O) 2960, 3000(C—H) 2550~3450(O—H) 1110, 1280(SO$_2$) | 2.45~2.95(2H, m)2.53(3H, s) 2.73(3H, s)3.20~3.35(H, m) 3.46(3H, s)3.63~3.86(H, m) 4.50~4.60(H, m)7.70(H, s) *2 |
| 25 | 1730(C=O) 2900, 2950, 3000(C—H) 2500~3500(O—H) 1125, 1285(SO$_2$) | 1.26(3H, t)2.30~2.90(2H, m) 2.54(3H, s)2.74(3H, s) 3.10~4.0(2H, m)3.54~3.88(2H, m) 4.62~4.68(H, m)7.69(H, s) *2 |
| 26 | 1730(C=O) 2900, 2960, 2980(C—H) 2600~3450(O—H) 1130, 1290(SO$_2$) | 0.92(3H, t)1.20~1.80(4H, m) 2.30~2.90(2H, m)2.58(3H, s) 2.77(3H, s)3.10~4.05(4H, m) 4.60~4.70(H, m)6.66(H, s, broad) 7.77(H, s) *2 |
| 27 | 1730(C=O) 2940, 2990(C—H) 2750~3450(O—H) 1110, 1285(SO$_2$) | 1.19~1.38(3H, m)2.56(3H, s) 2.74(3H, s)2.85~3.35(2H, m) 3.42(3H, s)3.85~4.05(H, m) 4.43~4.58(H, m)7.69(H, s) *2 |
| 28 | 1730(C=O) 2850, 2960(C—H) 2600~3500(O—H) 1140, 1300(SO$_2$) | 2.39(6H, s)2.30~2.80(2H, m) 3.10~3.90(2H, m)3.47(3H, m) 4.40~4.50(H, m) 7.64(H, m) *2 |
| 29 | — | 0.93(3H, t)1.40~1.85(2H, m) 2.40~3.05(2H, m)2.55(3H, s) 3.30~3.90(4H, m)4.75~4.85(H, m) 7.88(H, s) *3 |
| 30 | — | 1.24(6H, dd)2.30~2.55(H, m) 2.58(3H, s) 2.85~3.15(H, m)3.20~3.45(H, m) 3.53~3.77(H, m)3.87~4.20(H, m) 5.0~5.10(H, m)7.90(H, s) *3 |
| 31 | 1725(C=O) 2940, 2980(C—H) 2500~3450(O—H) 980(SO) | 1.24(3H, t)2.30~2.95(2H, m) 2.53(3H, s)2.70(3H, s) 3.05~3.50(2H, m)3.66(2H, q) 4.58~4.73(H, m)7.67(H, s) *2 |
| 32 | 1730(C=O) 2950, 3000(C—H) 2550~3450(O—H) 1140, 1300(SO$_2$) | 0.94(3H, t)1.40~1.85(2H, m) 2.45~3.0(2H, m)2.62(3H, s) 3.20~3.85(4H, m)4.80~4.90(H, m) 7.75(H, d)7.95(H, d) *3 |
| 33 | 1730(C=O) 2940, 2980(C—H) 2550~3450(O—H) 1120, 1305(SO$_2$) | 1.25(6H, dd)2.25~2.50(H, m) 2.65(3H, s)2.80~3.10(H, m) 3.20~3.50(H, m)3.55~3.75(H, m) 3.85~4.20(H, m)5.0~5.10(H, m) 7.75(H, d)7.95(H, d) *3 |

*1 KBr tablet method
*2 Solvent/deutero chloroform Internal standard/tetramethylsilane
*3 Solvent/deutero acetone Internal standard/tetramethylsilane Preparation Example 34

A 100-ml flask was charged with 1.0 g (0.0037 mol) of 4-methoxy-5-methylthiochroman-6-carboxylic acid-1,1-dioxide shown in Table 5, left column, and 5.0 ml of thionyl chloride, and the mixture was allowed to react at 60° C. for 30 minutes. After the reaction was completed, an excess of thionyl chloride was distilled off under reduced pressure. The remaining oil was dissolved in 5,0 ml of chloroform, and was added to a mixture of 0.41 g (0.0037 mol) of 1-ethyl-5-hydroxypyrazole, 0.37 g (0.0037 mol) of triethylamine and 20 ml of chloroform in another 200-ml flask, and the resultant mixture was allowed to react. After the mixture was allowed to react at room temperature for 2 hours, the reaction mixture was washed with 5 % hydrochloric acid and dried over anhydrous sodium sulfate, and the chloroform was distilled off under reduced pressure. Added to the remaining oil were 0.77 g (0.0056 mol) of anhydrous potassium carbonate and 1.0 ml of 1,4-dioxane, and the mixture was allowed to react at 130° C. for 2 hours. After allowed to cool, the reaction mixture was dissolved by adding 20 ml of water, and washed with ether. The aqueous layer was separated, and 5% hydrochloric acid was added to adjust the pH to 1. The precipitated oil was extracted with ethyl acetate, and the extract was dried over anhydrous sodium sulfate. Then, the ethyl acetate was distilled off under reduced pressure to give 4-methoxy-5-methyl-6-(1-ethyl-5-hydroxypyrazol-4-yl)carbonylthiochroman-1,1-dioxide (Compound 34) shown in Table 5, right column.

Preparation Examples 35–37

Compounds 35 to 37 of which the structural formulae are shown in Table 5, right column, were obtained in the same manner as in Preparation Example 34 except that the 4-methoxy-5-methylthiochroman-6-carboxylic acid-1,1-dioxide in Preparation Example 34 was replaced with starting materials shown in Table 5, left column.

Preparation Example 38

0.60 Gram of 5,8-dichloro-4-methoxy-6-(1,3-dimethyl-5-hydroxypyrazol-4-yl)carbonylthiochroman-1,1-dioxide (Compound 38) shown in Table 5 was obtained in the same manner as in Preparation Example 34 except that the 4-methoxy-5-methylthiochroman-6-carboxylic acid-1,1-dioxide in Preparation Example 34 was replaced with 5,8-dichloro-4-methoxythiochroman-6-carboxylic acid-1,1-dioxide and that the 1-ethyl-5-hydroxypyrazole in Preparation Example 34 was replaced with 1,3-dimethyl-5-hydroxypyrazole. The Yield thereof was 47%.

Preparation Example 39

4-Ethoxy-5-methyl-6-(1-ethyl-5-hydroxypyrazole-4-yl)carbonylthiochroman-1,1-dioxide (Compound 39) shown in Table 5, right column, was obtained in the same manner as in Preparation Example 34 except that the 4-methoxy-5-methylthiochroman-6-carboxylic acid-1,1-dioxide in Preparation Example 34 was replaced with a starting material shown in Table 5, left column.

Preparation Example 40

In a 50-ml flask, 0.70 g (0.0023 mol) of 8-fluoro-4-methoxy-2,5-dimethylthiochroman-6-carboxylic acid-1,1-dioxide, 0.28 g (0.0025 mol) of 1-ethyl-5-hydroxypyrazole and 0.52 g (0.0025 mol) of DCC (N,N'-dicyclohexylcarbodiimide) were added to 5 ml of tert-amyl alcohol at the same time, and the mixture was stirred at room temperature for 30 minutes. Then, 0.17 g (0.00125 mol) of anhydrous potassium carbonate was added. The reaction mixture was allowed to react at 80° C. for 8 hours, and then the reaction solvent was distilled off under reduced pressure. The remainder was dispersed in a 2% potassium carbonate aqueous solution and ethyl acetate to separate it into two phases. Further, the aqueous phase was acidified with 5% hydrochloric acid. and the precipitated oil was extracted with ethyl acetate. The extract was dried over anhydrous sodium sulfate and then concentrated under reduced pressure to give 0.70 g of 8-fluoro-4-methoxy-2,5-dimethyl-6-(1-ethyl-5-hydroxypyrazol-4-yl)carbonylthiochroman-1,1-dioxide (Compound 40) shown in Table 5. The yield thereof was 78%.

Preparation Examples 41, 53 and 56

Compounds 41, 53 and 56 of which the structural formulae are shown in Table 5, right column, were obtained in the same manner as in Preparation Example 40 except that the 6-fluoro-4-methoxy-2,5-dimethylthiochroman-6-carboxylic acid-1,1-dioxide in Preparation Example 40 was replaced with starting materials shown in Table 5, left column and that the 1-ethyl-5-hydroxypyrazole was replaced with 1,3-dimethyl-5-hydroxypyrazole.

Preparation Examples 42–52 and 55

Compounds 42 to 52 and 55 of which the structural formulae are shown in Table 5, right column, were obtained in the same manner as in Preparation Example 40 except that the 6-fluoro-4-methoxy-2,5-dimethylthiochroman-6-carboxylic acid-1,1-dioxide in Preparation Example 40 was replaced with starting materials shown in Table 5, left column.

Preparation Example 54

4-Methoxy-5-methyl-6-(1-methyl-5-hydroxypyrazole-4-yl)carbonylthiochroman-1,1-dioxide (Compound 54) shown in Table 5 was obtained in the same manner as in Preparation Example 40 except that the 6-fluoro-4-methoxy-2,5-dimethylthiochroman-6-carboxylic acid-1,1-dioxide in Preparation Example 40 was replaced with a starting material shown in Table 5 and that the 1-ethyl-5-hydroxypyrazole was replaced with 1-methyl-5-hydroxypyrazole.

Preparation Example 57

A 50-ml egg-plant type flask was charged with 1.7 g (0.0057 mol) of 4-methoxy-3,5,8-trimethylthiochroman-6-carboxylic acid-1,1-dioxide (Compound 27) and 0.64 g (0.0057 mol) of 1-ethyl-5-hydroxypyrazole, and then the mixture was suspended in 20 ml of methylene chloride. Then, 1.24 g (0.0060 mol) of DCC was added, and the mixture was allowed to react at room temperature for 8 hours. After the reaction was completed, insolubles were removed by filtration, and the methylene chloride was distilled off under reduced pressure to give an oil. This oil was purified by silica gel column chromatography to give 0.8 g of Compound A and 0.3 g of Compound B as a solid each. These Compounds were analyzed to show that Compound B was 3,4-trans-4-methoxy-3,5,8-trimethyl-6-(1-ethylpyrazol-4-yl)oxycarbonylthiochroman-1,1-dioxide and that Compound A was 3,4-cis-4-methoxy-3,5,8-trimethyl-6-(1-ethylpyrazol-4-yl)oxycarbonyl-thiochroman-1,1-dioxide. Table 4 shows the structures and physical properties of Compounds A and B.

TABLE 4

| Compd | Structural formula | Proton nuclear magnetic resonance spectrum* (ppm) |
|---|---|---|
| A | 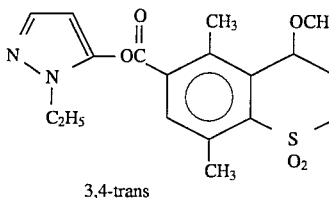<br>3,4-trans | 1.27(3H, d)1.44(3H, t)<br>2.63(3H, s)2.81(3H, s)<br>2.90–3.20(H, m)3.25–3.35(H, m)<br>3.45(3H, s)3.93(H, d)<br>4.09(2H, q)4.47(2H, d)6.24(H, d)<br>7.49(H, d)7.84(H, s) |
| B | 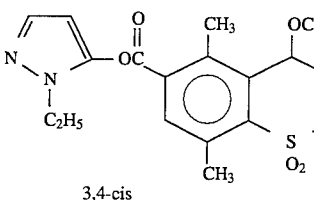<br>3,4-cis | 1.37(3H, d)1.44(3H, t)<br>2.67(3H, s)2.81(3H, s)<br>3.05–3.15(H, m)3.20–3.30(H, m)<br>3.48(3H, s)3.86(H, d)<br>4.09(2H, q)4.61(H, s)6.25(H, d)<br>7.49(H, d)7.84(H, s) |

*Solvent $CDCl_3$ Internal standard tetramethylsilane

A 50-ml egg-plant type flask was charged with 0.8 g (0.0020 mol) of Compound A and 0.41 g (0.003 mol) of potassium carbonate, and 2.0 ml of 1,4-dioxane was added. Then, the mixture was heated at 130° C. for 2 hours. After the reaction mixture was allowed to cool, the reaction mixture, 50 ml of ethyl acetate and 50 ml of a 5% potassium carbonate aqueous solution were added, and the aqueous layer was separated. Added to the aqueous layer was 5% hydrochloric acid to adjust the pH to 1, and the formed oil was extracted with methylene chloride. The extract was dried over sodium sulfate, and then the methylene chloride was distilled off under reduced pressure to give 0.8 g (0.0020 mol) of 3,4-trans-4-methoxy-3,5,8-trimethyl-6-(1-ethyl-5-hydroxypyrazol-4-yl)carbonylthiochroman-1,1-dioxide (Compound 57) shown in Table 5. The yield thereof from Compound 27 was 35%.

Preparation Example 58

A 50-ml egg-plant type flask was charged with 0.3 g (0.00076 mol) of Compound B and 0.16 g (0.0012 mol) of potassium carbonate, and 1.0 ml of 1,4-dioxane was added. Then, the mixture was heated at 130° C. for 2 hours. Thereafter, the reaction mixture was treated in the same manner as in Preparation Example 57 to give 0.24 g (0.00061 mol) of 3,4-cis-4-methoxy-3,5,8-trimethyl-6-(1-ethyl-5-hydroxypyrazol-4-yl)carbonylthiochroman-1,1-dioxide (Compound 58) shown in Table 5. The yield thereof from Compound B was 80%.

Preparation Example 59

A 50-ml egg-plant type flask was charged with 4.8 g (0.013 mol) of 8-fluoro-4-ethoxy-2,5-dimethyl-6-(1-ethyl-5-hydroxypyrazol-4-yl)carbonylthiochroman (Compound 43), 20 ml of acetic acid and 4.5 g (0.04 mol) of a 30% hydrogen peroxide aqueous solution, and the mixture was heated at 100° C. for 1 hour. After allowed to cool, the reaction mixture was poured into 100 ml of water. The precipitated oil was extracted with ethyl acetate, and the extract was dried over anhydrous sodium sulfate and then concentrated under reduced pressure to give 4.6 g of 8-fluoro-4-ethoxy-2,5-dimethyl-6-(1-ethyl-5-hydroxypyrazol-4-yl)carbonyl-thiochroman-1,1-dioxide (Compound 59) shown in Table 5.

Preparation Examples 60–62

Compounds 60 to 62 of which the structural formulae are shown in Table 5, right column, were obtained in the same manner as in Preparation Example 59 except that Compound 43 used as the starting material in Preparation Example 59 was replaced with starting materials shown in Table 5, left column.

Preparation Example 63

A 50-ml egg-plant type flask was charged with 0.50 g (0.0013 mol) of Compound 46 obtained in Preparation Example 46, 0.15 g (0.0013 mol) of a 30% hydrogen peroxide aqueous solution and 1.0 ml of acetic acid, and the mixture was allowed to react at room temperature for 3 days. After the reaction was completed 10 ml of a 1% sodium hydrogensulfite was added, and the mixture was extracted with methylene chloride. The solvent was distilled off under reduced pressure to give 0.47 g (0.0012 mol) of 5,8-dimethyl-4-methoxy-6-(1-ethyl-5-hydroxypyrazol-4-yl)-carbonylthiochroman-1-oxide (Compound 63) shown in Table 5. The yield thereof was 92%.

Preparation Example 64

0.60 Gram (0.0016 mol) of 8-fluoro-4-methoxy-5-methyl-6-(1-ethyl-5-hydroxypyrazol-4-yl)carbonylthiochroman-1,1-dioxide obtained in Preparation Example 35, 0.23 g (0.0020 mol) of methanesulfonyl chloride and 0.21 g (0.0021 mol) of triethylamine were mixed in 10 ml of methylene chloride, and then the mixture was stirred at room temperature for 2 days. The reaction mixture was diluted with methylene chloride, washed with water and further washed with a saturated sodium hydrogencarbonate aqueous solution. The washed reaction mixture was dried over anhydrous sodium sulfate, and the methylene chloride was distilled off under reduced pressure to give 0.20 g of 8-fluoro-4-methoxy-5-methyl-6-(1-ethyl-5-methanesulfonyl-oxypyrazol-4-yl)carbonylthiochroman-1,1-dioxide (Compound 64) shown in Table 5. The yield thereof was 28%.

Preparation Example 65

8-Fluoro-4-methoxy-5-methyl-6-(1-ethyl-5-p-toluenesulfonyloxypyrazol-4-yl)carbonylthiochroman-1,1-dioxide (Compound 65) shown in Table 5 was obtained in the same manner as in Preparation Example 64 except that the methanesulfonyl chloride in Preparation Example 64 was replaced with p-toluenesulfonyl chloride.

Preparation Example 66

0.70 Gram (0.0019 mol) of Compound 34 obtained in Preparation Example 34 was placed in a 100-ml egg-plant type flask, and 20 ml of methylene chloride was added to dissolve Compound 34. Then, a solution of 0.30 g (0.002 mol) of potassium carbonate in 30 ml of water was added. Further, 0.55 g (0.0029 mol) of p-toluenesulfonyl chloride and 0.05 g (0.00022 mol) of benzyltriethylammonium chloride were added. The mixture was allowed to react at room temperature for 3 hours, and further refluxed under heat for 3 hours. After the reaction mixture was allowed to cool, the methylene chloride layer was separated and dried over sodium sulfate. The solvent was removed under reduced pressure to obtain an oil, and the oil was purified by silica gel column chromatography to give 0.70 g (0.0014 mol) of 4-methoxy-5-methyl-6-(1-ethyl-5-p-toluenesulfonyloxypyrazol-4-yl)-carbonylthiochroman-1,1-dioxide (Compound 66) shown in Table 5. The yield thereof was 74%.

Preparation Example 67

4-Methoxy-5-methyl-6-(1-ethyl-5-n-propane-sulfonyloxypyrazol-4-yl)carbonylthiochroman-1,1-dioxide (Compound 67) shown in Table 5 was obtained in the same manner as in Preparation Example 66 except that the p-toluenesulfonyl chloride in Preparation Example 66 was replaced with n-propanesulfonyl chloride.

Preparation Example 68

4-Methoxy-5,8-dimethyl-6-(1-ethyl-5-p-toluenesulfonyloxypyrazol-4-yl)carbonylthiochroman-1,1-dioxide (Compound 68) shown in Table 5 was obtained in the same manner as in Preparation Example 66 except that Compound 34 used as the starting material in Preparation Example 66 was replaced with Compound 47.

Preparation Example 69

4-Methoxy-5,8-dimethyl-6-(1-ethyl-5-n-propanesulfonyloxypyrazol-4-yl)carbonylthiochroman (Compound 69) shown in Table 5 was obtained in the same manner as in Preparation Example 66 except that Compound 34 used as the starting material in Preparation Example 66 was replaced with Compound 46 and that the p-toluenesulfonyl chloride was replaced with n-propanesulfonyl chloride.

Preparation Example 70

4-Methoxy-5,8-dimethyl-6-(1-ethyl-5-p-chlorobenzenesulfonyloxypyrazol-4-yl)carbonylthiochroman (Compound 70) shown in Table 5 was obtained in the same manner as in Preparation Example 69 except that the n-propanesulfonyl chloride in Preparation Example 69 was replaced with p-chlorobenzenesulfonyl chloride.

Preparation Example 71

4-Methoxy-5,8-dimethyl-6-(1-ethyl-5-i-butanesulfonyloxypyrazol-4-yl)carbonylthiochroman-1,1-dioxide (Compound 71) shown in Table 5 was obtained in the same manner as in Preparation Example 68 except that the p-toluenesulfonyl chloride in Preparation Example 68 was replaced with i-butanesulfonyl chloride.

Preparation Example 72

4-Methoxy-5,8-dimethyl-6-(1-ethyl-5-benzenesulfonyloxypyrazol-4-yl)carbonylthiochroman-1,1-dioxide (Compound 72) shown in Table 5 was obtained in the same manner as in Preparation Example 68 except that the p-toluenesulfonyl chloride in Preparation Example 68 was replaced with benzenesulfonyl chloride.

Preparation Example 73

4-Methoxy-5,8-dimethyl-6-(1-ethyl-5-(2,5-dichlorobenzenesulfonyl)oxypyrazol-4-yl)carbonylthiochroman-1,1-dioxide (Compound 73) shown in Table 5 was obtained in the same manner as in Preparation Example 68 except that the p-toluenesulfonyl chloride in Preparation Example 68 was replaced with 2,5-dichlorobenzenesulfonyl chloride.

Preparation Example 74

A 50-ml egg-plant type flask was charged with 1.1 g (0.0024 mol) of Compound 69 obtained in Preparation Example 69, 3.0 ml of acetic acid and 0.70 g (0.0062 mol) of a 30% hydrogen peroxide aqueous solution, and the mixture was heated at 80° C. for 3 hours. After the reaction mixture was allowed to cool, 30 ml of a 1% sodium hydrogensulfite aqueous solution was added, and the mixture was extracted with methylene chloride. The methylene chloride layer was washed with a saturated sodium bicarbonate aqueous solution and dried over sodium sulfate. The methylene chloride was distilled under reduced pressure to give 0.85 g (0.0018 mol) of 4-methoxy-5,8-dimethyl-6-(1-ethyl-5-n-propanesulfonyl-oxypyrazol-4-yl)carbonylthiochroman-1,1-dioxide (Compound 74) shown in Table 5. The yield thereof was 75%.

Preparation Example 75

A 50-ml egg-plant type flask was charged with 1.2 g (0.0025 mol) of Compound 70 obtained in Preparation Example 70, 3.0 ml of acetic acid and 0.71 g (0.0063 mol) of a 30% hydrogen peroxide aqueous solution, and the mixture was heated at 80° C. for 3 hours. After the reaction mixture was allowed to cool, 30 ml of a 1% sodium hydrogensulfite aqueous solution was added, and the mixture was extracted with methylene chloride. The methylene chloride layer was washed with a saturated sodium bicarbonate aqueous solution and dried over sodium sulfate. The methylene chloride was distilled under reduced pressure to give 0.99 g (0.0019 mol) of 4-methoxy-5,8-dimethyl-6-(1-ethyl-5-p-chlorobenzene-sulfonyloxypyrazol-4-yl)carbonylthiochroman-1,1-dioxide (Compound 75) shown in Table 5 The yield thereof was 76%.

Preparation Example 76

A 50-ml egg-plant type flask was charged with 0.5 g (0.0010 mol) of Compound 70 obtained in Preparation Example 70, 1.0 ml of acetic acid and 0.15 g (0.0013 mol) of a 30% hydrogen peroxide aqueous solution, and the mixture was allowed to react at room temperature for 24 hours. After the reaction was completed, 30 ml of a 1% sodium hydrogensulfite aqueous solution was added, and the mixture was extracted with methylene chloride. The methylene chloride layer was washed with a saturated sodium bicarbonate aqueous solution and dried over sodium sulfate. The methylene chloride was distilled under reduced pressure to give 0.44 g (0.00087 mol) of 4-methoxy-5,8-dimethyl-6-(1-ethyl-5-p-chlorobenzenesulfonyloxypyrazol-4-yl)carbonyl-thiochroman-1-oxide (Compound 76) shown in Table 5. The yield thereof was 87%.

Preparation Example 77

A 50-ml egg-plant type flask was charged with 0.75 g (0.0022 mol) of Compound 56 obtained in Preparation Example 56, 2.0 ml of acetic acid and 0.62 g (0.0055 mol) of a 30% hydrogen peroxide aqueous solution, and the mixture was allowed to react at 80° C. for 2 hours. After the reaction was completed, 20 ml of a 1% sodium hydrogensulfite aqueous solution was added, and the mixture was extracted with methylene chloride. The methylene chloride layer was dried over sodium sulfate. The methylene chloride was distilled under reduced pressure to give 0.78 g (0.0021 mol) of 4-methoxy-5,8-dimethyl-6-(1,3-dimethyl-5-hydroxypyrazol-4-yl)carbonylthiochroman-1,1-dioxide (Compound 77) shown in Table 5 The yield thereof was 95%.

Preparation Example 78

0.63 Gram (0.0017 mol) of Compound 77 obtained in Preparation Example 77 was placed in a 100-ml egg-plant type flask, and 20 ml of methylene chloride was added to dissolve Compound 77. Then, a solution of 0.28 g (0.002 mol) of potassium carbonate in 30 ml of water was added. Further, 0.55 g (0.0029 mol) of p-toluenesulfonyl chloride and 0.05 g (0.00022 mol) of benzyltriethylammonium chloride were added. The mixture was allowed to react at room temperature for 3 hours, and further refluxed under heat for 3 hours. After the reaction mixture was allowed to cool, the methylene chloride layer was separated and dried over sodium sulfate. The solvent was removed under reduced pressure to obtain an oil, and the oil was purified by silica gel column chromatography to give 0.40 g (0.00075 mol) of 4-methoxy-5,8-dimethyl-6-(1,3-dimethyl-5-p-toluenesulfonyloxypyrazol-4-yl)-carbonylthiochroman-1,1-dioxide (Compound 78) shown in Table 5. The yield thereof was 44%.

Table 5 shows the structures and yields of Compounds 34 to 78 obtained in the above Examples 34 to 78, and Table 6 shows the physical properties thereof.

TABLE 5

| Prep. Ex. No. | Starting material | Prepd Compd No. | Structural formula | Yield (%) |
|---|---|---|---|---|
| 34 | | 34 | | 65 |
| 35 | | 35 | | 72 |
| 36 | | 36 | | 53 |
| 37 | | 37 | | 43 |

TABLE 5-continued

| Prep. Ex. No. | Starting material | Prepd Compd No. | Structural formula | Yield (%) |
|---|---|---|---|---|
| 38 | | 38 | | 47 |
| 39 | | 39 | | 52 |
| 40 | | 40 | | 78 |
| 41 | | 41 | | 39 |
| 42 | | 42 | | 73 |
| 43 | | 43 | | 64 |
| 44 | | 44 | | 40 |
| 45 | | 45 | | 53 |

TABLE 5-continued

| Prep. Ex. No. | Starting material | Prepd Compd No. | Structural formula | Yield (%) |
|---|---|---|---|---|
| 46 | (structure) | 46 | (structure) | 50 |
| 47 | (structure) | 47 | (structure) | 75 |
| 48 | (structure) | 48 | (structure) | 54 |
| 49 | (structure) | 49 | (structure) | 74 |
| 50 | (structure) | 50 | (structure) | 84 |
| 51 | (structure) | 51 | (structure) | 64 |
| 52 | (structure) | 52 | (structure) | 77 |
| 53 | (structure) | 53 | (structure) | 37 |

TABLE 5-continued

| Prep. Ex. No. | Starting material | Prepd Compd No. | Structural formula | Yield (%) |
|---|---|---|---|---|
| 54 | (structure) | 54 | (structure) | 68 |
| 55 | (structure) | 55 | (structure) | 76 |
| 56 | (structure) | 56 | (structure) | 25 |
| 57 | (structure) | 57 | (structure, 3,4-trans form) | 35 |
| 58 | (structure, 3,4-cis form) | 58 | (structure, 3,4-cis form) | 80 |
| 59 | (structure) | 59 | (structure) | 85 |
| 60 | (structure) | 60 | (structure) | 100 |

TABLE 5-continued

| Prep. Ex. No. | Starting material | Prepd Compd No. | Structural formula | Yield (%) |
|---|---|---|---|---|
| 61 | | 61 | | 97 |
| 62 | | 62 | | 92 |
| 63 | | 63 | | 92 |
| 64 | | 64 | | 28 |
| 65 | | 65 | | 22 |
| 66 | | 66 | | 74 |
| 67 | | 67 | | 95 |

TABLE 5-continued

| Prep. Ex. No. | Starting material | Prepd Compd No. | Structural formula | Yield (%) |
|---|---|---|---|---|
| 68 | | 68 | | 82 |
| 69 | | 69 | | 78 |
| 70 | | 70 | | 85 |
| 71 | | 71 | | 86 |
| 72 | | 72 | | 71 |

TABLE 5-continued

| Prep. Ex. No. | Starting material | Prepd Compd No. | Structural formula | Yield (%) |
|---|---|---|---|---|
| 73 | | 73 | | 50 |
| 74 | | 74 | | 75 |
| 75 | | 75 | | 76 |
| 76 | | 76 | | 87 |
| 77 | | 77 | | 95 |

TABLE 5-continued

| Prep. Ex. No. | Starting material | Prepd Compd No. | Structural formula | Yield (%) |
|---|---|---|---|---|
| 78 | (structure: pyrazole with CH₃, N-CH₃, OH, linked via C=O to benzene ring bearing CH₃, CH₃, OCH₃, and fused thiochroman with SO₂) | 78 | (structure: same core with O-SO₂-C₆H₄-CH₃ (tosylate) replacing OH) | 44 |

TABLE 6

| Compd No. | Infrared absorption spectrum *1 (cm⁻¹) | Proton nuclear magnetic resonance spectrum *2 (ppm) |
|---|---|---|
| 34 | 1630(C=O) 2840, 2950, 2990(C—H) 2500–3450(O—H) 1135, 1295, 1315(SO₂) | 1.47(3H, t)2.4–2.9(2H, m)2.44(3H, s)3.1–3.8(2H, m)3.50(3H, s)4.08(2H, q)4.50–4.65(H, m)5.4(H, s, broad)7.32(H, s) 7.57(H, d)7.92(H, d) |
| 35 | 1630(C=O) 2830, 2950, 2955(C—H) 2600–3450(O—H) 1135, 1295, 1315(SO₂) | 1.47(3H, t)2.37(3H, s) 2.5–3.0(2H, m)3.1–3.9(2H, m) 3.50(3H, s)4.08(2H, q) 4.42–4.60(H, m)6.7(H, s, broad)7.28(H, d)7.35(H, s)7.72(H, d) |
| 36 | 1640(C=O) 2850, 2970, 3010(C—H) 25.00–3480(O—H) 1140, 1325, 1340(SO₂) | 1.46(3H, t)2.5– 2.8(2H, m)3.2–3.9(2H, m)3.51(3H, s)4.08(2H, q)4.71–4.83(H, m)5.60(H, broad)7.35(H, s)7.56(H, s) |
| 37 | 1630(C=O) 2830, 2950, 2990(C—H) 2600–3450(O—H) 1130, 1295, 1315(SO₂) | 1.34(3H, t)2.3–2.7(2H, m) 2.36(3H, s)3.0–3.6(2H, m) 3.50(3H, s)3.99(H, q) 4.64–4.80(H, m)7.53(H, s) 7.90(H, s) |
| 38 | 1640(C=O) 2850, 2970, 3010(C—H) 2600–3500(O—H) 1140, 1305, 1325(SO₂) | 1.83(3H, s)2.3–3.0(2H, m) 3.4–4.0(2H, m)3.52(3H, s)3.56(3H, s)4.79–4.94(H, m)7.70(H, s) |
| 39 | 1620(C=O) 2940, 2980(C—H) 3200–3500(O—H) 1120, 1285, 1305(SO₂) | 1.21(3H, t)1.40(3H, t) 2.4–3.1(2H, m)2.42(3H, s) 3.2–3.7(2H, m)3.5–4.0(2H, m)4.05(2H, q)4.79–4.86(H, m)7.38(H, s)7.59–7.87(2H, m) |
| 40 | 1630(C=O) 2850, 2950(C—H) 2500–3450(O—H) 1140, 1295(SO₂) | 1.30–1.70(6H, m)2.36(3H, s) 2.40–2.75(2H, m) 3.2–4.0(H, m)3.49(3H, s)4.08(2H, q)4.4i–4.57(H, m)6.95(H, s, broad.)7.25(H, d)7.30(H, d) |
| 41 | 1630(C=O) 2860, 2950(C—H) 2600–3450(O—H) 1130, 1285, 1315(SO₂) | 1.50–1.70(3H, m)1.72(3H, s) 2.2–2.8(3H, m)2.27(3H, s)3.47(3H, s)3.64(3H, s)3.25–3.95(H, m)4.40–4.55(H, m)5.10(H, S, broad.)7.10(H, d) |
| 42 | 1630(C=O) 2850, 3000(C—H) 2500–3450(O—H) | 1.37–1.55(6H, m)1.6–1.8(H, m)2.24–2.74(2H, m)2.36(3H, s)3.45(3H, s)4.06(2H, q)4.47–4.68(H, m)7.08(H, d) 7.40(H, s)7.87(H, s, broad) |
| 43 | 1630(C=O) 2890, 2950, 2990(C—H) 2500–3450(O—H) | 1.18–1.54(9H, m)1.6–1.8(H, m)2.10–2.75(2H, m)2.40(3H, s)3.35–3.92(2H, m)4.08(2H, q)4.60–4.73(H, m)6.40(H, s, broad)7.10(H, d)7.42(H, s) |
| 44 | 1630(C=O) 2840, 2950, 2990(C—H) 2500–3200(O—H) | 1.14–1.50(6H, m)1.8–2.2(H, m)2.55–2.85(H, m)3.1–3.8(H, m)3.48(3H, s) 3.90–4.25(2H, m)4.5–4.9(H, m)7.40–7.83(2H, m) *2 |
| 45 | 1630(C=O) 2850, 2950, 3000(C—H) 2500–3450(O—H) 1130, 1300(SO₂) | 0.93(3H, t)1.35–1.85(2H, m)1.40(3H, t)2.30–2.95(2H, m)2.43(3H, s)3.35–3.90(4H, m)4.06(2H, q)4.47–4.87(H, m)5.3(H, s, broad)7.39(H, s) 7.65(H, d)7.83(H, d) *3 |
| 46 | 1630(C=O) 2840, 2960, 3000(C—H) 2600–3150(O—H) | 1.45(3H, t)1.68–1.96(H, m) 2.25(3H, s)2.41(3H, s) 2.64–2.93(2H, m) 3.10–3.33(H, m)3.45(3H, s) 4.06(2H, q)4.50–4.60(H, m) 7.20(H, s)7.41(H, s)7.64(H, s, broad) *2 |
| 47 | 1630(C=O) 2850, 2960, 3000(C—H) 2500–3450(O—H) 1130, 1300, 1320(SO₂) | 1.45(3H, t)2.36(3H, s) 2.46–2.90(2H, m)2.75(3H, s) 3.10–3.90(2H, m)3.47(3H, s) 4.09(2H, q)4.50–4.58(H, m) 7.0(H, s, broad)7.28–7.34(2H, m) *2 |
| 48 | 1620(C=O) 2850, 2960, 3000(C—H) 2600–3100(O—H) | 1.45(3H, t)1.6–1.9(H, m)2.5–3.0(2H, m)3.1–3.4(H, m)3.43(3H, s)4.08(2H, q)4.70–4.80(H, m)7.30(H, dd)7.62(H, m)8.6(H, s, broad) *2 |
| 49 | 1620(C=O) 2870, 2930, 2980(C—H) 2600–3200(O—H) | 1.26(3H, t)1.45(3H, t) 1.66–1.96(H, m)2.24(3H, s)2.41(3H, s)2.62–2.86(2H, m)3.15–3.60(H, m) 3.75(2H, q)4.06(2H, q)4.60–4.72(H, m)6.85(H, s, broad) 7.19(H, s)7.42(H, s) *2 |
| 50 | 1630(C=O) 2940, 2980(C—H) 3100–3450(O—H) 1125, 1285, 1310(SO₂) | 1.26(3H, t)1.46(3H, t)2.38(3H, s)2.47–2.85(2H, m)2.77(3H, s)3.1–4.0(2H, m)3.63(2H, q)4.08(2H, q)4.58–4.68(H, m)6.60(H, s, broad)7.31(H, s)7.34(H, s) *2 |
| 51 | 1620(C=O) 2930, 2970(C—H) 2400–3300(O—H) | 1.22(3H, t)1.45(3H, t)1.6–2.0(H, m)2.4–3.1(2H, m)3.2–3.4(H, m)3.5–3.9(2H, m)4.07(2H, q)4.80–4.90(H, m)7.30(H, dd)7.61(H, d) 8.2(H, s, broad) *2 |
| 52 | 1630(C=O) 2890, 2960(C—H) 2400–3500(O—H) | 0.91(3H, t)1.20–1.54(7H, m)2.38(3H, s)2.48–2.90(2H, m)2.77(3H, s)3.10–4.15(4H, |

TABLE 6-continued

| Compd No. | Infrared absorption spectrum *1 (cm$^{-1}$) | Proton nuclear magnetic resonance spectrum *2 (ppm) |
|---|---|---|
|  | 1130, 1290, 1310(SO$_2$) | m)4.08(2H, q)4.56~4.66(H, m)5.2(H, s, broad) 7.28~7.35(2H, m) *2 |
| 53 | 1620(C=O) 2930(C—H) 2600~3450(O—H) 1120, 1285, 1305(SO$_2$) | 1.67(3H, s)2.35(3H, s)2.4~2.7(2H, m)2.8~3.8(2H, m)3.48(3H, s)3.55(3H, s)4.66~4.76(H, m)5.8(H, s, broad)7.50(H, d)7.83(H, d) *3 |
| 54 | 1640(C=O) 2960, 3000(C—H) 2600~3500(O—H) 1135, 1295, 1315(SO$_2$) | 2.3~2.7(2H, m)2.40(3H, s) 2.85~3.85(2H, m)3.50(3H, s)3.66(3H, s)4.67~4.76(H, m)5.5(H, s, broad)7.35(H, s)7.63(H, d)7.83(H, d) *3 |
| 55 | 1630(C=O) 2940, 2980(C—H) 2600~3450(O—H) 1130~1310(SO$_2$) | 1.12~1.51(9H, m)2.26~2.67(2H, m)2.48(3H, s)2.80~3.45(2H, m)3.55~3.80(H, m)3.90~4.0(H, m)4.07(2H, q)4.3(H, s, broad) 5.0~5.10(H, m)7.38(H, s) 7.64(H, d)7.83(H, d) *2 |
| 56 | 1635(C=O) 2960(C—H) 2600~3450(O—H) | 1.52~1.94(H, m)1.77(3H, s) 2.24(3H, s)2.30(3H, s)2.56~2.94(2H, m)3.08~3.32(H, m)3.44(3H, s)3.62(3H, s) 4.45~4.55(H, m)6.95(H, s) 7.6(H, s, broad) *2 |
| 57 | 1620(C=O) 2940, 2980(C—H) 2600~3450(O—H) 1150, 1290(SO$_2$) | 1.27(3H, d)1.46(3H, t)2.39(3H, s)2.76(3H, s)2.84~3.35(2H, m)3.43(3H, s)3.60~3.97(H, m)4.08(2H, q)4.36~4.48(H, m)6.16(H, s, broad)7.26~7.35(2H, m) *2 |
| 58 | 1630(C=O) 2960, 2950, 2980(C—H) 2400~3250(O—H) 1125, 1295(SO$_2$) | 1.35(3H, d)1.46(3H, t)2.44(3H, s)2.77(3H, s)2.83~3.27(2H, m)3.46(3H, s)3.75~3.95(H, m)4.08(2H, q)4.47~4.55(H, m)6.04(H, s, broad)7.27~7.33(2H, m) *2 |
| 59 | 1635(C=O) 2890, 2950, 3000(C—H) 3300~3450(O—H) 1140, 1290, 1320(SO$_2$) | 1.2~1.6(9H, m)2.1~2.8(2H, m)2.37(3H, s)3.45~4.30(3H, m)4.10(2H, q)4.5 5~4.65(H, m)7.26~7.74(2H, m)8.4(H, s, broad) |
| 60 | 1650(C=O) 2960, 3000(C—H) 2500~3200(O—H) 1140, 1275, 1315(SO$_2$) | 1.12~1.47(6H, m)2.5~3.3(2H, m)3.40~3.52(3H, m)3.7~4.0(H, m)4.04(2H, q)4.62~4.85(H, m)7.32~7.87(2H, m) |
| 61 | 1640(C=O) 2850, 2960, 3000(C—H) 2600~3450(O—H) 1140, 1300, 1325(SO$_2$) | 1.45(3H, t)2.6~2.8(2H, m) 3.2~4.0(2H, m)3.47(3H, s)4.10(2H, q)4.65~4.80(H, m)7.4~7.9(H, m)7.55(H, d)9.2(H, s, broad) |
| 62 | 1630(C=O) 2950, 2990(C—H) 2400~3300(O—H) 1130, 1320(SO$_2$) | 1.23(3H, t)1.47(3H, t)2.4~2.8(2H, m)3.1~3.9(4H, m)4.10(2H, m)4.76~4.90(H, m)7.1(H, s, broad)7.3~7.9(H, m)7.55(H, d) |
| 63 | 1630(C=O) 2830, 2940, 2990(C—H) 2600~3450(O—H) 1000(SO) | 1.45(3H, t)2.37(3H, s) 2.52~2.80(2H, m)2.73(3H, s) 3.18~3.90(2H, m)3.48(3H, s) 4.07(2H, q)4.48~4.54(H, m) 6.5(H, s, broad)7.31(2H, s) |
| 64 | 1660(C=O) 2960, 3000(C—H) 1130, 1300(SO$_2$) 1200, 1400(OSO$_2$) | 1.52(3H, t)2.30(3H, d)2.5~2.9(2H, m)3.1~4.0(2H, m)3.48(3H, s)3.62(3H, s)4.23(2H, q)4.44~4.55(H, m)7.20(H, d)7.45(H, s) *2 |
| 65 | 1660(C=O) 2950, 2990(C—H) 1140, 1300(SO$_2$) 1190, 1400(OSO$_2$) | 1.50(3H, t)2.29(3H, s)2.47(3H, s)2.50~2.70(2H, m)3.12~3.90(2H, m)3.47(3H, s)4.16(2H, q)4.54~4.64(H, m)7.00(H, d)7.36(H, s)7.50(2H, d)7.82(2H, d) *3 |
| 66 | 1665(C=O) | 1.43(3H, t)2.36(3H, |
| 67 | 1660(C=O) 2850, 2960, 3000(C—H) 1140, 1300(SO$_2$) 1205, 1380(OSO$_2$) | s)2.48(3H, s)2.67~2.97(2H, m)3.35~3.70(2H, m)3.53(3H, s)4.12(2H, q)4.66~4.75(H, m)7.40~7.82(7H, m) *3 1.18(3H, t)1.50(3H, t)1.86~2.30(2H, m)2.37(3H, s)2.54~2.84(2H, m)3.12~3.78(2H, m)3.48(3H, s)3.65(2H, t)4.50~4.60(H, m)7.47(H, s) 7.50(H, d)7.89(H, d) *2 |
| 68 | 1660(C=O) 2940(C—H) 1125, 1290, 1310(SO$_2$) 1180, 1390(OSO$_2$) | 1.51(3H, t)2.29(3H, s)2.46(3H, s)2.64~2.94(2H, m)2.69(3H, s)3.10~3.90(2H, m)3.46(3H, s)4.20(2H, q)4.45~4.55(H, m)7.06(H, s)7.34(H, s)7.48(2H, d) 7.84(2H, d) *2 |
| 69 | 1660(C=O) 2850, 2970, 3000(C—H) 1185, 1395(OSO$_2$) | 1.14(3H, t)1.51(3H, t)1.66~1.88(H, m)1.85~2.20(2H, m)2.24(3H, m)2.35(3H, s)2.56~2.90(2H, m)3.08~3.33(H, m)3.44(3H, s)3.60(2H, t) 4.21(2H, q)4.48~4.58(H, m) 7.10(H, s)7.56(H, s) |
| 70 | 1665(C=O) 2850, 2970, 3000(C—H) 1205, 1400(OSO$_2$) | 1.54(3H, t)1.64~1.93(H, m)2.15(3H, s)2.30(3H, s)2.60~2.90(2H, m)3.12~3.33(H, m)3.45(3H, s)4.25(2H, q)4.48~4.58(H, m)6.92(H, s)7.51(2H, d)7.60(H, s)7.85(2H, d) |
| 71 | 1665(C=O) 2960, 2990(C—H) 1130, 1300(SO$_2$) 1185, 1385(OSO$_2$) | 1.20(6H, d)1.51(3H, t) 2.25~2.90(3H, m)2.31(3H, s) 2.75(3H, s)3.10~4.0(2H, m) 3.48(3H, s)3.61(2H, d)4.22(2H, q)4.45~4.55(H, m)7.23(H, s)7.49(H, s) |
| 72 | 1665(C=O) 2830, 2950, 2990(C—H) 1130, 1290(SO$_2$) 1200, 1390(OSO$_2$) | 1.51(3H, t)2.20~2.95(2H, m) 2.28(3H, s)2.68(3H, s) 3.10~3.40(H, m)3.45(3H, s) 3.62~4.02(H, m)4.20(2H, q) 4.45~4.55(H, m)7.07(H, s) 7.53~8.01(6H, m) |
| 73 | 1660(C=O) 2830, 2950, 3000(C—H) 1130, 1295(SO$_2$) 1200, 1400(OSO$_2$) | 1.55(3H, t)2.18(3H, s)2.40~2.90(2H, m)2.70(3H, s)3.10~3.35(H, m)3.45(3H, s)3.65~4.05(H, m)4.26(2H, q)4.50~4.60(H, m)7.03(H, s) 7.43(H, s)7.57~7.59(2H, m) 7.92~7.95(H, m) |
| 74 | 1660(C=O) 2820, 2940, 2980(C—H) 1120, 1285, 1305(SO$_2$) 1170, 1375(OSO$_2$) | 1.17(3H, t)1.51(3H, t)1.90~2.30(2H, m)2.32 (3H, s)2.48~2.90(2H, m)2.75(3H, s)3.12~3.90(2H, m)3.46(3H, s)4.22(2H, q)4.45~4.55(H, m)7.23(H, s)7.47(H, s) |
| 75 | 1665(C=O) 2830, 2950, 2990(C—H) 1130, 1290, 1310(SO$_2$) 1195, 1405(OSO$_2$) | 1.53(3H, t)2.26(3H, s)2.45~2.90(2H, m)2.71(3H, s)3.13~3.88(2H, m)3.45(3H, s)4.23(2H, q)4.45~4.55(H, m)7.08(H, s)7.51(H, s)7.59(2H, d)7.95(2H, d) |
| 76 | 1665(C=O) 2840, 2960, 3000(C—H) 1040(SO) 1200, 1410(OSO$_2$) | 1.53(3H, t)2.25(3H, s)2.53~2.75(2H, m)2.68(3H, s)3.03~3.35(2H, m)3.47(3H, s)4.24(2H, q)4.44~4.55(H, m)7.09(H, s)7.47(H, s)7.59(H, d)7.97(2H, d) |
| 77 | 1630(C=O) 2840, 2960, 3000(C—H) 2600~3450(O—H) 1125, 1290(SO$_2$) | 1.70(3H, s)2.09(3H, s) 2.29(3H, s)2.50~2.90(2H, m) 3.10~4.0(2H, m)3.46(3H, s) 3.64(3H, s)4.45~4.55(H, m) 7.14(H, s)8.8(H, s, broad) |
| 78 | 1665(C=O) 2840, 2950(C—H) | 2.15~2.90(2H, m)2.27(3H, s) 2.38(3H, s)2.46(3H, |

TABLE 6-continued

| Compd No. | Infrared absorption spectrum *1 (cm$^{-1}$) | Proton nuclear magnetic resonance spectrum *2 (ppm) |
|---|---|---|
| | 1130, 1290(SO$_2$) 1190, 1400(OSO$_2$) | s)2.60(3H, s)3.15–4.10(2H, m)4.50–4.60(H, m)3.47(3H, s)3.71(3H, s)7.04(H, s)7.42(4H, dd) |

*1 KBr tablet method
*2 Solvent/deutero chloroform Internal standard/tetramethylsilane
*3 Solvent/deutero acetone Internal standard/tetramethylsilane

REFERENTIAL EXAMPLE

As Referential Example, the synthesis of 6-bromo-5-methylthiochroman-4-one used as the starting material in Preparation Example 1 will be described below.

Referential Example (Synthesis of 6-bromo-5-methyl-thiochroman-4-one)

A one-liter, three-necked flask was charged with 50 g (0.4 mol) of m-toluenethiol, 29 g (0.4 mol) of acrylic acid and 1.0 ml of triethylamine, and the mixture was allowed to react at 150° C. for 1 hour. After the reaction mixture was allowed to cool, 200 ml of acetic acid was added to the reaction mixture, and the mixture was heated up to 50° C. to form a complete solution. Then, 21 ml of bromine was gradually added over 30 minutes, and the mixture was further allowed to react at 50° to 60° C. for 1 hour. After the reaction was completed, the reaction mixture was poured into 1.5 liters of a 1% sodium hydrogensulfide aqueous solution, and the formed solid was recovered by filtration and dried to give 110 g of 3-(4-bromo-3-methylphenylthio)-propionic acid as a crude product.

27.5 Grams (0.1 mol) of the above-obtained crude 3-(4-bromo-3-methylphenylthio)propionic acid was charged into a one-liter, three-necked flask, and 200 ml of dichloromethane was added to form a complete solution. Then, 100 ml of concentrated sulfuric acid was added over 30 minutes, and the mixture was allowed to react for 1 hour by refluxing it under heat. After allowed to cool, the reaction mixture was poured into 1 liter of water, and the mixture was extracted with dichloromethane. The dichloromethane layer was washed with a saturated sodium bicarbonate aqueous solution, and dried over sodium sulfate. The dichloromethane Was distilled off under reduced pressure, and the remainder was purified by silica gel column chromatography to give 4.4 g of 6-bromo-5-methylthiochroman-4-one. The yield thereof was 17%.

NMR (ppm, solvent CDCl$_3$, internal standard tetramethylsilane)

2.62 (3H,s) 2.92–3.30 (4H,m) 7.00 (H,d) 7.50 (H,d)

Herbicide Examples 1–69 and Herbicide Comparative Examples 1–4

(1) Preparation of Herbicide

97 Parts by weight of talc (trade name: Zeaklite) as a carrier, 1.5 parts by weight of alkylarylsulfonate (trade name: Neoplex, supplied by Kao-Atlas K.K.) as a surfactant and 1.5 parts by weight of a nonionic and anionic surfactant (trade name: Sorpol 800A, supplied by Toho Chemical Co., Ltd.) were uniformly pulverized and mixed to obtain a carrier for a wettable powder.

90 Parts by weight of the above carrier and 10 parts by weight of one compound of the present invention obtained in any one of the above Preparation Examples (or 10 parts by weight of pyrazolate for Herbicide Comparative Examples 1 and 3 or 10 parts by weight of the compound described in JP-A-63-122672 for Herbicide Comparative Examples 2 and 4) were uniformly pulverized and mixed obtain a herbicide.

(2) Biological Test (Foliar treatment test, Herbicide Examples 1–45 and Comparative Examples 1 and 2)

Seeds of weeds such as crabgrass, barnyardgrass, green foxtail, cocklebur, velvetleaf and slender amaranth and seeds of corn, wheat and barley were sown in 1/5,000-are Wagner pots filled with upland soil, and covered with upland soil. Then, the seeds were grown in a greenhouse, and when they grew to plants at one or two-leaved stage, a predetermined amount of the herbicide prepared in the above (1) was suspended in water and uniformly sprayed to foliar portions at a rate of 200 liters/10 are. Thereafter, the plants were grown in the greenhouse, and 20 days after the treatment, the herbicide was determined for herbicidal efficacy. Table 7 shows the results.

The herbicidal efficacy and the phytotoxicity to the crops are shown on the basis of the following ratings.

| (Ratings) Herbicidal efficacy | Ratio of remaining plant weight to non-treated [%] |
|---|---|
| 0 | 81–100 |
| 1 | 61–80 |
| 2 | 41–60 |
| 3 | 21–40 |
| 4 | 1–20 |
| 5 | 0 |

| Phytotoxicity | Ratio of remaining plant weight to non-treated [%] |
|---|---|
| − | 100 |
| ± | 95–99 |
| + | 90–94 |
| ++ | 80–89 |
| +++ | 0–79 |

TABLE 7

| No. | Compound used | Dosage [g$^{a.i.}$/are] | Herbicidal efficacy Crab- grass | Barnyard- glass | Green foxtail | Cockle- bur | Herbicidal efficacy Velvet- leaf | Slender amaranth | Phytotoxicity Corn | Wheat | Barley |
|---|---|---|---|---|---|---|---|---|---|---|---|
| Herbicide Example 1 | No. 34 | 10 | 5 | 5 | 5 | 5 | 5 | 5 | — | — | — |
| Herbicide Example 1 | " | 3 | 5 | 5 | 5 | 5 | 5 | 5 | — | — | — |
| Herbicide | No. 35 | 10 | 5 | 5 | 5 | 5 | 5 | 5 | — | — | — |

TABLE 7-continued

| No. | Compound used | Dosage [g^{n.i.}/are] | Herbicidal efficacy | | | | Herbicidal efficacy | | Phytotoxicity | | |
|---|---|---|---|---|---|---|---|---|---|---|---|
| | | | Crab-grass | Barnyard-glass | Green foxtail | Cockle-bur | Velvet-leaf | Slender amaranth | Corn | Wheat | Barley |
| Herbicide Example 2 | " | 3 | 5 | 5 | 5 | 5 | 5 | 5 | — | — | — |
| Herbicide Example 3 | No. 36 | 10 | 5 | 5 | 5 | 5 | 5 | 5 | — | — | — |
| Herbicide Example 3 | " | 3 | 5 | 5 | 5 | 5 | 5 | 5 | — | — | — |
| Herbicide Example 4 | No. 37 | 10 | 5 | 5 | 5 | 5 | 5 | 5 | — | — | — |
| Herbicide Example 4 | " | 3 | 5 | 5 | 5 | 5 | 5 | 5 | — | — | — |
| Herbicide Example 5 | No. 38 | 10 | 5 | 5 | 5 | 5 | 5 | 5 | — | — | — |
| Herbicide Example 5 | " | 3 | 4 | 5 | 5 | 5 | 5 | 5 | — | — | — |
| Herbicide Example 6 | No. 39 | 10 | 5 | 5 | 5 | 5 | 5 | 5 | — | — | — |
| Herbicide Example 6 | " | 3 | 5 | 5 | 5 | 5 | 5 | 5 | — | — | — |
| Herbicide Example 7 | No. 40 | 10 | 5 | 5 | 5 | 5 | 5 | 5 | — | — | — |
| Herbicide Example 7 | " | 3 | 5 | 4 | 5 | 5 | 5 | 5 | — | — | — |
| Herbicide Example 8 | No. 41 | 10 | 5 | 5 | 5 | 5 | 5 | 5 | — | — | — |
| Herbicide Example 8 | " | 3 | 5 | 4 | 4 | 4 | 5 | 5 | — | — | — |
| Herbicide Example 9 | No. 42 | 10 | 5 | 5 | 5 | 5 | 5 | 5 | — | — | — |
| Herbicide Example 9 | " | 3 | 4 | 4 | 4 | 4 | 4 | 4 | — | — | — |
| Herbicide Example 10 | No. 43 | 10 | 5 | 5 | 5 | 5 | 5 | 5 | — | — | — |
| Herbicide Example 10 | " | 3 | 4 | 4 | 4 | 4 | 5 | 5 | — | — | — |
| Herbicide Example 11 | No. 44 | 10 | 5 | 4 | 4 | 4 | 5 | 5 | — | — | — |
| Herbicide Example 11 | " | 3 | 4 | 4 | 4 | 4 | 4 | 4 | — | — | — |
| Herbicide Example 12 | No. 45 | 10 | 5 | 5 | 5 | 5 | 5 | 5 | — | — | — |
| Herbicide Example 12 | " | 3 | 5 | 5 | 5 | 5 | 5 | 5 | — | — | — |
| Herbicide Example 13 | No. 46 | 10 | 5 | 5 | 5 | 5 | 5 | 5 | — | — | — |
| Herbicide Example 13 | " | 3 | 5 | 5 | 5 | 5 | 5 | 5 | — | — | — |
| Herbicide Example 14 | No. 47 | 10 | 5 | 5 | 5 | 5 | 5 | 5 | — | — | — |
| Herbicide Example 14 | " | 3 | 5 | 5 | 5 | 5 | 5 | 5 | — | — | — |
| Herbicide Example 15 | No. 48 | 10 | 4 | 5 | 4 | 4 | 5 | 5 | — | — | — |
| Herbicide Example 15 | " | 3 | 4 | 4 | 4 | 4 | 5 | 5 | — | — | — |
| Herbicide Example 16 | No. 49 | 10 | 5 | 5 | 5 | 5 | 5 | 5 | — | — | — |
| Herbicide Example 16 | " | 3 | 4 | 4 | 5 | 5 | 5 | 5 | — | — | — |
| Herbicide Example 17 | No. 50 | 10 | 5 | 5 | 5 | 5 | 5 | 5 | — | — | — |
| Herbicide Example 17 | " | 3 | 5 | 5 | 5 | 5 | 5 | 5 | — | — | — |
| Herbicide Example 18 | No. 51 | 10 | 5 | 5 | 5 | 5 | 5 | 5 | — | — | — |
| Herbicide Example 18 | " | 3 | 5 | 5 | 5 | 5 | 5 | 5 | — | — | — |
| Herbicide Example 19 | No. 52 | 10 | 4 | 4 | 5 | 4 | 5 | 5 | — | — | — |
| Herbicide Example 19 | " | 3 | 4 | 4 | 4 | 4 | 5 | 5 | — | — | — |
| Herbicide Example 20 | No. 53 | 10 | 5 | 5 | 5 | 5 | 5 | 5 | — | — | — |

TABLE 7-continued

| | | | Herbicidal efficacy | | | Herbicidal efficacy | | Phytotoxicity | | |
|---|---|---|---|---|---|---|---|---|---|---|
| No. | Compound used | Dosage [g$^{a.i.}$/are] | Crab-grass | Barnyard-glass | Green foxtail | Cockle-bur | Velvet-leaf | Slender amaranth | Corn | Wheat | Barley |
| Herbicide Example 20 | " | 3 | 4 | 4 | 5 | 5 | 4 | 5 | — | — | — |
| Herbicide Example 21 | No. 54 | 10 | 5 | 5 | 5 | 5 | 5 | 5 | — | — | — |
| Herbicide Example 21 | " | 3 | 5 | 5 | 5 | 5 | 4 | 4 | — | — | — |
| Herbicide Example 22 | No. 55 | 10 | 5 | 5 | 5 | 5 | 5 | 5 | — | — | — |
| Herbicide Example 22 | " | 3 | 5 | 5 | 5 | 5 | 5 | 5 | — | — | — |
| Herbicide Example 23 | No. 56 | 10 | 5 | 5 | 5 | 5 | 5 | 5 | — | — | — |
| Herbicide Example 23 | " | 3 | 4 | 5 | 5 | 5 | 5 | 5 | — | — | — |
| Herbicide Example 24 | No. 57 | 10 | 5 | 5 | 5 | 5 | 5 | 5 | — | — | — |
| Herbicide Example 24 | " | 3 | 5 | 5 | 5 | 5 | 5 | 5 | — | — | — |
| Herbicide Example 25 | No. 58 | 10 | 5 | 5 | 5 | 5 | 5 | 5 | — | — | — |
| Herbicide Example 25 | " | 3 | 5 | 5 | 5 | 5 | 5 | 5 | — | — | — |
| Herbicide Example 26 | No. 59 | 10 | 5 | 5 | 5 | 5 | 5 | 5 | — | — | — |
| Herbicide Example 26 | " | 3 | 4 | 5 | 4 | 5 | 5 | 5 | — | — | — |
| Herbicide Example 27 | No. 60 | 10 | 5 | 5 | 5 | 5 | 5 | 5 | — | — | — |
| Herbicide Example 27 | " | 3 | 5 | 4 | 4 | 5 | 5 | 5 | — | — | — |
| Herbicide Example 28 | No. 61 | 10 | 5 | 5 | 5 | 5 | 5 | 5 | — | — | — |
| Herbicide Example 28 | " | 3 | 5 | 4 | 4 | 5 | 5 | 5 | — | — | — |
| Herbicide Example 29 | No. 62 | 10 | 5 | 5 | 5 | 5 | 5 | 5 | — | — | — |
| Herbicide Example 29 | " | 3 | 5 | 5 | 5 | 5 | 5 | 5 | — | — | — |
| Herbicide Example 30 | No. 63 | 10 | 5 | 5 | 5 | 5 | 5 | 5 | — | — | — |
| Herbicide Example 30 | " | 3 | 5 | 5 | 5 | 5 | 5 | 5 | — | — | — |
| Herbicide Example 31 | No. 64 | 10 | 5 | 5 | 5 | 5 | 5 | 5 | — | — | — |
| Herbicide Example 31 | " | 3 | 4 | 5 | 4 | 5 | 5 | 5 | — | — | — |
| Herbicide Example 32 | No. 65 | 10 | 5 | 5 | 5 | 5 | 5 | 5 | — | — | — |
| Herbicide Example 32 | " | 3 | 4 | 5 | 5 | 5 | 5 | 5 | — | — | — |
| Herbicide Example 33 | No. 66 | 10 | 5 | 5 | 5 | 5 | 5 | 5 | — | — | — |
| Herbicide Example 33 | " | 3 | 4 | 5 | 4 | 5 | 5 | 5 | — | — | — |
| Herbicide Example 34 | No. 67 | 10 | 5 | 5 | 5 | 5 | 5 | 5 | — | — | — |
| Herbicide Example 34 | " | 3 | 5 | 5 | 5 | 5 | 5 | 5 | — | — | — |
| Herbicide Example 35 | No. 68 | 10 | 5 | 5 | 5 | 5 | 5 | 5 | — | — | — |
| Herbicide Example 35 | " | 3 | 5 | 5 | 5 | 5 | 5 | 5 | — | — | — |
| Herbicide Example 36 | No. 69 | 10 | 4 | 4 | 5 | 5 | 5 | 4 | — | — | — |
| Herbicide Example 36 | " | 3 | 4 | 4 | 4 | 5 | 4 | 4 | — | — | — |
| Herbicide Example 37 | No. 70 | 10 | 4 | 4 | 5 | 5 | 5 | 4 | — | — | — |
| Herbicide Example 37 | " | 3 | 4 | 4 | 4 | 4 | 4 | 4 | — | — | — |
| Herbicide Example 38 | No. 71 | 10 | 5 | 5 | 5 | 5 | 5 | 5 | — | — | — |
| Herbicide | " | 3 | 4 | 4 | 5 | 5 | 5 | 5 | — | — | — |

TABLE 7-continued

| No. | Compound used | Dosage [g$^{a.i.}$/are] | Herbicidal efficacy | | | | | | Phytotoxicity | | |
|---|---|---|---|---|---|---|---|---|---|---|---|
| | | | Crab- grass | Barnyard- glass | Green foxtail | Cockle- bur | Velvet- leaf | Slender amaranth | Corn | Wheat | Barley |
| Example 38 Herbicide | No. 72 | 10 | 5 | 5 | 5 | 5 | 5 | 5 | — | — | — |
| Example 39 Herbicide | " | 3 | 4 | 4 | 5 | 4 | 4 | — | — | — | — |
| Example 39 Herbicide | No. 73 | 10 | 4 | 4 | 4 | 5 | 5 | 5 | — | — | — |
| Example 40 Herbicide | " | 3 | 4 | 4 | 4 | 4 | 5 | 4 | — | — | — |
| Example 40 Herbicide | No. 74 | 10 | 5 | 5 | 5 | 5 | 5 | 5 | — | — | — |
| Example 41 Herbicide | " | 3 | 4 | 5 | 4 | 5 | 5 | 4 | — | — | — |
| Example 41 Herbicide | No. 75 | 10 | 5 | 5 | 5 | 5 | 5 | 5 | — | — | — |
| Example 42 Herbicide | " | 3 | 5 | 5 | 5 | 5 | 5 | 5 | — | — | — |
| Example 42 Herbicide | No. 76 | 10 | 5 | 5 | 5 | 5 | 5 | 5 | — | — | — |
| Example 43 Herbicide | " | 3 | 5 | 4 | 5 | 5 | 4 | 4 | — | — | — |
| Example 43 Herbicide | No. 77 | 10 | 5 | 5 | 5 | 5 | 5 | 5 | — | — | — |
| Example 44 Herbicide | " | 3 | 5 | 4 | 5 | 5 | 4 | 4 | — | — | — |
| Example 44 Herbicide | No. 78 | 10 | 5 | 5 | 5 | 5 | 4 | 5 | — | — | — |
| Example 45 Herbicide | " | 3 | 4 | 4 | 5 | 5 | 4 | 4 | — | — | — |
| Example 45 Herbicide Comparative Example 1 | x | 10 | 0 | 0 | 0 | 0 | 0 | 1 | — | — | — |
| Herbicide Comparative Example 2 | y | 3 | 0 | 0 | 0 | 3 | 3 | 2 | — | — | — | a.i. = abbreviation for active ingredient

Compound x: Comparative Example 1 (Commercially available herbicide, pyrazolate)

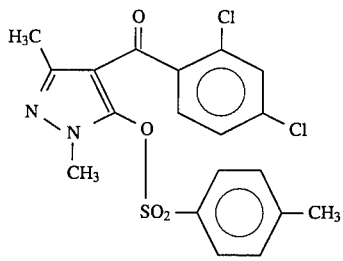

Compound y: Comparative Example 2 (Compound described in JP-A-63-122672)

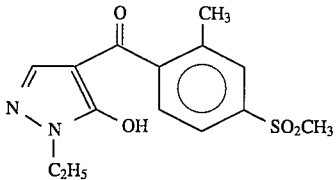

3) Biological test (Soil treatment test on upland soil, Herbicide Examples 46–69 and Comparative Examples 3 and 4)

Seeds of weeds such as crabgrass, barnyardgrass, green foxtail, cocklebur, velvetleaf and slender amaranth and seeds of corn, wheat and barley were sown in 1/5,000 are Wagner pots filled with upland soil, and covered with upland soil. Then, a predetermined amount of the herbicide prepared in the above (1) was suspended in water and uniformly sprayed onto the soil surface. Thereafter, the seeds were grown in a greenhouse, and 20 days after the treatment, the herbicide was determined for herbicidal efficacy. Table 8 shows the results.

The herbicidal efficacy and the phytotoxicity to the crops are shown according to the basis described in (2) foliar treatment test.

TABLE 8

| No. | Compound used | Dosage [g^a.i./are] | Herbicidal efficacy | | | | Herbicidal efficacy | | Phytotoxicity | | |
|---|---|---|---|---|---|---|---|---|---|---|---|
| | | | Crab-grass | Barnyard-glass | Green foxtail | Cockle-bur | Velvet-leaf | Slender amaranth | Corn | Wheat | Barley |
| Herbicide Example 46 | No. 34 | 10 | 5 | 5 | 5 | 5 | 5 | 5 | — | — | — |
| Herbicide Example 46 | " | 3 | 5 | 4 | 5 | 4 | 5 | 5 | — | — | — |
| Herbicide Example 47 | No. 37 | 10 | 5 | 5 | 5 | 5 | 5 | 5 | — | — | — |
| Herbicide Example 47 | " | 3 | 4 | 5 | 4 | 4 | 5 | 5 | — | — | — |
| Herbicide Example 48 | No. 39 | 10 | 5 | 5 | 5 | 5 | 5 | 5 | — | — | — |
| Herbicide Example 48 | " | 3 | 5 | 5 | 5 | 5 | 5 | 5 | — | — | — |
| Herbicide Example 49 | No. 45 | 10 | 5 | 5 | 5 | 5 | 5 | 5 | — | — | — |
| Herbicide Example 49 | " | 3 | 5 | 4 | 5 | 5 | 5 | 5 | — | — | — |
| Herbicide Example 50 | No. 47 | 10 | 5 | 5 | 5 | 5 | 5 | 5 | — | — | — |
| Herbicide Example 50 | " | 3 | 4 | 5 | 5 | 5 | 5 | 5 | — | — | — |
| Herbicide Example 51 | No. 50 | 10 | 5 | 5 | 5 | 5 | 5 | 5 | — | — | — |
| Herbicide Example 51 | " | 3 | 4 | 5 | 4 | 5 | 5 | 5 | — | — | — |
| Herbicide Example 52 | No. 53 | 10 | 5 | 5 | 5 | 5 | 5 | 5 | — | — | — |
| Herbicide Example 52 | " | 3 | 5 | 5 | 5 | 5 | 5 | 5 | — | — | — |
| Herbicide Example 53 | No. 54 | 10 | 5 | 5 | 5 | 5 | 5 | 5 | — | — | — |
| Herbicide Example 53 | " | 3 | 5 | 5 | 5 | 4 | 5 | 5 | — | — | — |
| Herbicide Example 54 | No. 55 | 10 | 5 | 5 | 5 | 5 | 5 | 5 | — | — | — |
| Herbicide Example 54 | " | 3 | 5 | 5 | 5 | 5 | 5 | 5 | — | — | — |
| Herbicide Example 55 | No. 57 | 10 | 5 | 5 | 5 | 5 | 5 | 5 | — | — | — |
| Herbicide Example 55 | " | 3 | 5 | 5 | 5 | 5 | 5 | 5 | — | — | — |
| Herbicide Example 56 | No. 58 | 10 | 5 | 5 | 5 | 5 | 5 | 5 | — | — | — |
| Herbicide Example 56 | " | 3 | 5 | 5 | 4 | 4 | 5 | 5 | — | — | — |
| Herbicide Example 57 | No. 59 | 10 | 5 | 5 | 5 | 5 | 5 | 5 | — | — | — |
| Herbicide Example 57 | " | 3 | 5 | 4 | 5 | 5 | 5 | 5 | — | — | — |
| Herbicide Example 58 | No. 63 | 10 | 5 | 5 | 5 | 5 | 5 | 5 | — | — | — |
| Herbicide Example 58 | " | 3 | 5 | 5 | 5 | 4 | 5 | 5 | — | — | — |
| Herbicide Example 59 | No. 66 | 10 | 5 | 5 | 5 | 5 | 5 | 5 | — | — | — |
| Herbicide Example 59 | " | 3 | 5 | 5 | 4 | 4 | 5 | 5 | — | — | — |
| Herbicide Example 60 | No. 67 | 10 | 5 | 5 | 5 | 5 | 5 | 5 | — | — | — |
| Herbicide Example 60 | " | 3 | 5 | 5 | 5 | 5 | 5 | 5 | — | — | — |
| Herbicide Example 61 | No. 68 | 10 | 5 | 5 | 5 | 5 | 5 | 5 | — | — | — |
| Herbicide Example 61 | " | 3 | 5 | 5 | 4 | 4 | 5 | 5 | — | — | — |
| Herbicide Example 62 | No. 71 | 10 | 5 | 5 | 5 | 5 | 5 | 5 | — | — | — |
| Herbicide Example 62 | " | 3 | 5 | 5 | 5 | 4 | 5 | 5 | — | — | — |
| Herbicide Example 63 | No. 72 | 10 | 5 | 5 | 5 | 5 | 5 | 5 | — | — | — |
| Herbicide Example 63 | " | 3 | 5 | 5 | 5 | 5 | 5 | 5 | — | — | — |
| Herbicide | No. 73 | 10 | 5 | 5 | 5 | 5 | 5 | 5 | — | — | — |

TABLE 8-continued

| No. | Compound used | Dosage [g a.i./are] | Herbicidal efficacy | | | | Herbicidal efficacy | | Phytotoxicity | | |
|---|---|---|---|---|---|---|---|---|---|---|---|
| | | | Crab- grass | Barnyard- glass | Green foxtail | Cockle- bur | Velvet- leaf | Slender amaranth | Corn | Wheat | Barley |
| Herbicide Example 64 | " | 3 | 5 | 5 | 5 | 4 | 5 | 5 | — | — | — |
| Herbicide Example 64 | No. 74 | 10 | 5 | 5 | 5 | 5 | 5 | 5 | — | — | — |
| Herbicide Example 65 | " | 3 | 5 | 5 | 5 | 5 | 5 | 5 | — | — | — |
| Herbicide Example 65 | No. 75 | 10 | 5 | 5 | 5 | 5 | 5 | 5 | — | — | — |
| Herbicide Example 66 | " | 3 | 5 | 5 | 5 | 5 | 5 | 5 | — | — | — |
| Herbicide Example 66 | No. 76 | 10 | 5 | 5 | 5 | 5 | 5 | 5 | — | — | — |
| Herbicide Example 67 | " | 3 | 5 | 5 | 5 | 5 | 5 | 5 | — | — | — |
| Herbicide Example 67 | No. 77 | 10 | 5 | 5 | 5 | 5 | 5 | 5 | — | — | — |
| Herbicide Example 88 | " | 3 | 5 | 5 | 4 | 4 | 5 | 5 | — | — | — |
| Herbicide Example 88 | No. 78 | 10 | 5 | 5 | 5 | 5 | 5 | 5 | — | — | — |
| Herbicide Example 69 | " | 3 | 5 | 5 | 4 | 4 | 5 | 5 | — | — | — |
| Herbicide Comparative Example 3 | x | 10 | 0 | 0 | 0 | 0 | 0 | 0 | — | — | — |
| Herbicide Comparative Example 4 | y | 3 | 3 | 2 | 2 | 0 | 0 | 0 | — | — | — | a.i. = abbreviation for active ingredient

Compound x: Comparative Example 3 (Commercially available herbicide, pyrazolate)

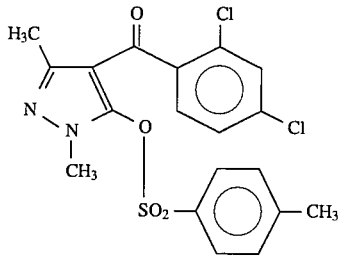

Compound y: Comparative Example 4 (Compound described in JP-A-63-122672)

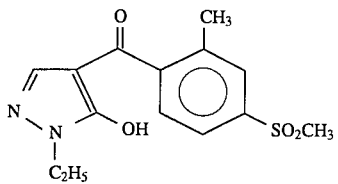

Effects of the Invention

As detailed above, according to the present invention, there has been provided the novel pyrazole derivative which shows high selectivity to corn, wheat and barley and which is capable of controlling gramineous weeds and broad-leaved weeds together at a low dosage, the process for the production of the above novel pyrazole derivative, the herbicide containing the above novel pyrazole derivative as an active ingredient, and the novel intermediate compound suitable for the production of the above novel pyrazole derivative.

What is claimed is:

1. A process for the production of a pyrazole compound, the process comprising reacting a compound of the formula (II)

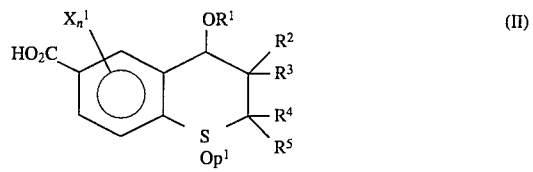

wherein $R^1$ is a $C_1$–$C_6$ alkyl group, each of $R^2$, $R^3$, $R^4$ and $R^5$ is independently hydrogen or a $C_1$–$C_4$ alkyl group, $X^1$ is a $C_1$–$C_4$ alkyl group or a halogen atom, n is an integer of 1 to 3, and $p^1$ is an integer of 0 to 2, with a compound of the formula (III)

wherein $R^6$ is a $C_1$–$C_4$ alkyl group, and $R^7$ is hydrogen or a $C_1$–$C_4$ alkyl group, to form a pyrazole compound of the formula (Ia),

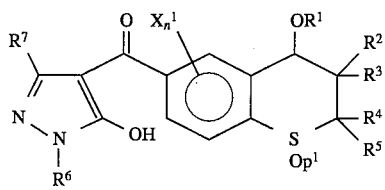

(Ia)

wherein $R^1$, $R^2$, $R^3$, $R^4$, $R^5$, $R^6$, $R^7$, $X^1$, n and $p^1$ are as defined above,
and optionally reacting the pyrazole compound (Ia) with a sulfonic acid halide of the formula (IV).

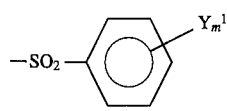

(IV)

wherein $Q^2$ is —$SO_2$—$R^8$ or

—$SO_2$—⟨⟩—$Y_m^1$ in which $R^8$ is a $C_1$–$C_6$ alkyl group,
Y is hydrogen, a $C_1$–$C_4$ alkyl group or a halogen atom, and
$m^1$ is an integer of 1 to 3, and
$X^2$ is a halogen atom
to obtain a pyrazole compound of the formula (Ib),

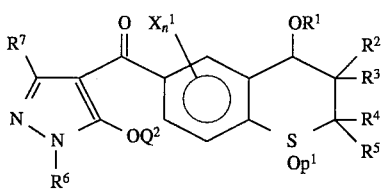

(Ib)

wherein $R^1$, $R^2$, $R^3$, $R^4$, $R^5$, $R^6$, $R^7$, $X^1$, n, $p^1$ $Q^2$, $R^8$, Y and $m^1$ are as defined above.

2. A process for the production of a pyrazole compound, the process comprising reacting a compound of the formula (II)

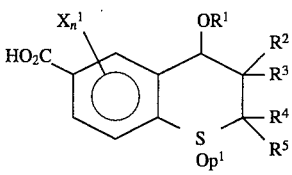

(II)

wherein $R^1$ is a $C_1$–$C_6$ alkyl group,
each of $R^2$, $R^3$, $R^4$ and $R^5$ is independently hydrogen or a $C_1$–$C_4$ alkyl group,
$X^1$ is a $C_1$–$C_4$ alkyl group or a halogen atom,
n is an integer of 1 to 3, and
$p^1$ is an integer of 0 to 2,
with a halogenation agent to form a compound of the formula (V)

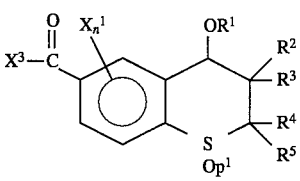

(V)

wherein $R^1$, $R^2$, $R^3$, $R^4$, $R^5$, $X^1$, n and $p^1$ are as defined above and $X^3$ is a halogen atom, then reacting the above compound (V) with a compound of the formula (III)

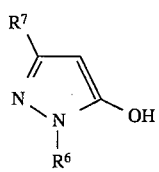

(III)

wherein $R^6$ is a $C_1$–$C_4$ alkyl group, and
$R^7$ is hydrogen or a $C_1$–$C_4$ alkyl group, to form a compound of the formula (VI)

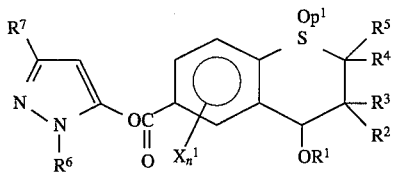

(VI)

wherein $R^1$, $R^2$, $R^3$, $R^4$, $R^5$, $R^6$, $R^7$, $X^1$, n and $p^1$ are as defined above,
then heating the compound (VI) to form a pyrazole compound of the general formula (Ia)

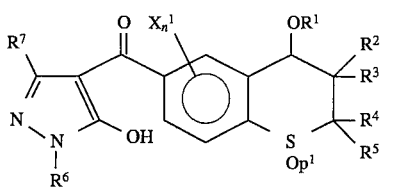

(Ia)

wherein $R^1$, $R^2$, $R^3$, $R^4$, $R^5$, $R^6$, $R^7$, $X^1$, n and $p^1$ are as defined above,
and optionally reacting the pyrazole compound (Ia) with a sulfonic acid halide of the formula (IV)

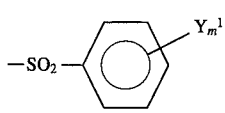

(IV)

wherein $Q^2$ is —$SO_2$—$R^8$ or

—$SO_2$—⟨⟩—$Y_m^1$ in which $R^8$ is a $C_1$–$C_6$ alkyl group,
Y is hydrogen, a $C_1$–$C_4$ alkyl group or a halogen atom, and
$m^1$ is an integer of 1 to 3, and
$X^2$ is a halogen atom, to obtain a pyrazole compound of the formula (Ib)

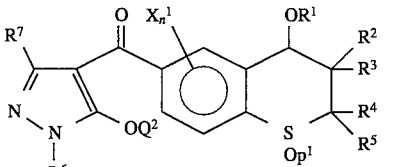

(Ib)

wherein $R^1$, $R^2$, $R^3$, $R^4$, $R^5$, $R^6$, $R^7$, $X^1$, n, $p^1$, $Q^2$, $R^8$, Y and $m^1$ are as defined above.

3. A process for the production of a pyrazole compound of the general formula (Ic)

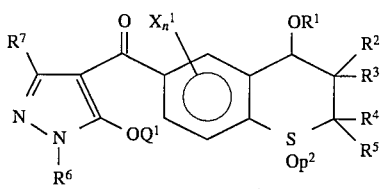

wherein $R^1$ is a $C_1$–$C_6$ alkyl group,
each of $R^2$, $R^3$, $R^4$ and $R^5$ is independently hydrogen or a $C_1$–$C_4$ alkyl group,
$R^6$ is a $C_1$–$C_4$ alkyl group,
$R^7$ is hydrogen or a $C_1$–$C_4$ alkyl group,
$X^1$ is a $C_1$–$C_4$ alkyl group or a halogen atom,
n is an integer of 1 to 3,
$p^2$ is 1 or 2, and
$Q^1$ is hydrogen, —$SO_2$–$R^8$ or

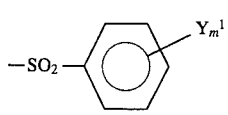

in which $R^8$ is a $C_1$–$C_6$ alkyl group,
Y is hydrogen, a $C_1$–$C_4$ alkyl group or a halogen atom, and
$m^1$ is an integer of 1 to 3,
the process comprising oxidizing a pyrazole compound of the formula (Id)

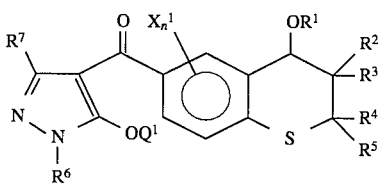

wherein $R^1$, $R^2$, $R^3$, $R^4$, $R^5$, $R^6$, $R^7$, $X^1$, n, $Q^1$, $R^8$, Y and $m^1$ are as defined above.

4. The process of claim 1, wherein a molar ratio of the compound of formula (II) to the compound of formula (III) is 1:1 to 1:3.

5. The process of claim 4, wherein the reacting of the compound of the formula (II) and the compound (III) takes place in the presence of:
  (i) 1.0 to 1.5 moles of N,N'-dicyclohexylcarbodiimide per mole of the compound of the formula (II),
  (ii) 0.5 to 2.0 moles of a base per mole of the compound of the formula (II) and the compound of the formula (III), wherein the base is selected from the group consisting of potassium carbonate and sodium carbonate, and
  (iii) an inert solvent selected from the group consisting of tert-butyl alcohol, tert-amyl alcohol and i-propyl alcohol,
and is carried out at a temperature of 50° to 100° C.

6. The process of claim 5, wherein a molar ratio of the compound of the formula (Ia) to the compound of the formula (IV) is 1:1 to 1:10.

7. The process of claim 6, wherein the reacting of the compound of the formula (Ia) and the compound of the formula (IV) takes place in the presence of:
  (i) an inert solvent selected from the group consisting of diethyl ether, tetrahydrofuran, dichloromethane and chloroform and (ii) a phase transfer catalyst selected from the group consisting of crown ether and benzyltriethylammonium chloride.

8. The process of claim 2, wherein the halogenating agent is selected from the group consisting of thionyl chloride and phosphorus oxychloride, and the halogenating agent being in an amount greater than an equimolar amount of the compound of the formula (II).

9. The process of claim 8, wherein a molar ratio of the compound of the formula (V) to the compound of the formula (III) is 1:1 to 1:3.

10. The process of claim 9, wherein the reacting of the compound of the formula (V) with the compound of the formula (III) is in the presence of:
  (i) a solvent selected from the group consisting of dioxane, acetonitrile, benzene, toluene, chloroform, methylene chloride and 1,2-dichloroethane, and
  (ii) a base selected from the group consisting of sodium hydroxide, potassium hydroxide, sodium carbonate, potassium carbonate, triethylamine and pyridine,
and is carried out at a temperature of 0° to 60° C.

11. The process of claim 10, wherein the compound of the formula (VI) is heated at a temperature of 80° to 150° C. in the presence of a base selected from the group consisting of sodium carbonate, potassium carbonate and triethylamine, the base being in an amount of at least equimolar to the amount of the compound of the formula (VI).

12. The process of claim 10, wherein a molar ratio of the compound of the formula (Ia) to the compound of the formula (IV) is 1:1 to 1:10.

13. The process of claim 10, wherein the reacting of the compound of the formula (Ia) with the compound of the formula (Ib) is carried out in the presence of:
  (i) an inert solvent selected from the group consisting of diethyl ether, tetrahydrofuran, dichloromethane and chloroform,
  (ii) a base selected from the group consisting of sodium carbonate, potassium carbonate, triethylamine and pyridine, and
  (iii) a phase transfer catalyst selected from the group consisting of crown ether and benzyltriethylammonium chloride.

14. The process of claim 3, wherein the oxidizing agent is selected from the group consisting of hydrogen peroxide, peracetic acid and sodium metaperiodate.

15. The process of claim 14, wherein the oxidizing agent is hydrogen peroxide and the process is carried out in the presence of acetic acid.

16. A compound of the formula (II)

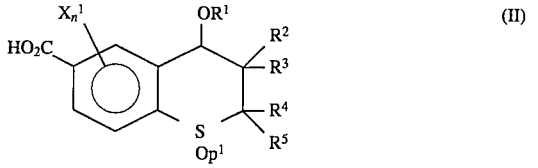

wherein $R^1$ is a $C_1$–$C_6$ alkyl group,
each of $R^2$, $R^3$, $R^4$ and $R^5$ is independently hydrogen or a $C_1$–$C_4$ alkyl group,
$X^1$ is a $C_1$–$C_4$ alkyl group or a halogen atom,
n is an integer of 1 to 3, and
$p^1$ is an integer of 0 to 2.

17. The compound of the formula (II) which is selected from the group consisting of

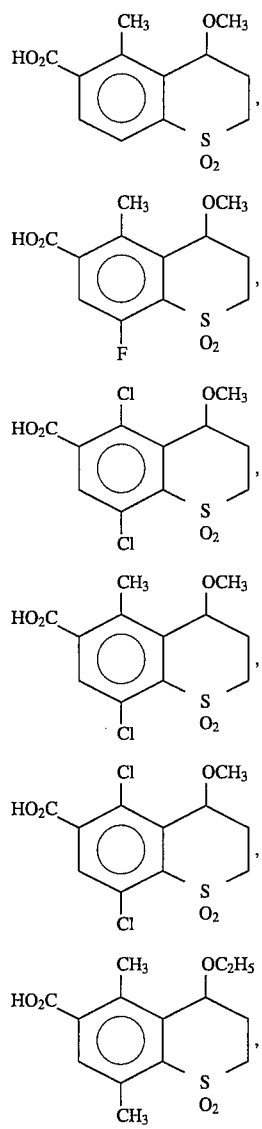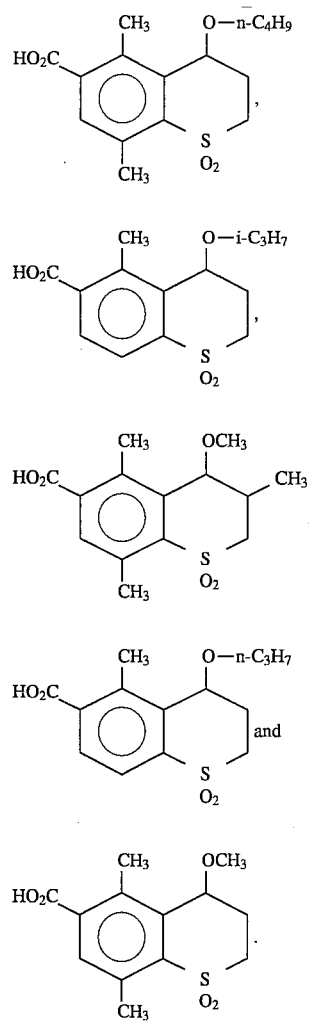
* * * * *